//

US008129547B2

(12) United States Patent
Hellstern et al.

(10) Patent No.: US 8,129,547 B2
(45) Date of Patent: Mar. 6, 2012

(54) ANTICOAGULATION OF HUMAN BLOOD EX VIVO

(76) Inventors: Peter Hellstern, Bobenheim-Roxheim (DE); Jörg Stürzebecher, Erfurt-Rhoda (DE); Uta Stürzebecher, legal representative, Erfurt-Rhoda (DE)

( * ) Notice: Subject to any disclaimer, the term of this patent is extended or adjusted under 35 U.S.C. 154(b) by 875 days.

(21) Appl. No.: 12/223,280

(22) PCT Filed: Jan. 26, 2007

(86) PCT No.: PCT/EP2007/000661
§ 371 (c)(1),
(2), (4) Date: Jul. 25, 2008

(87) PCT Pub. No.: WO2007/085461
PCT Pub. Date: Aug. 2, 2007

(65) Prior Publication Data
US 2010/0280412 A1    Nov. 4, 2010

(30) Foreign Application Priority Data

Jan. 26, 2006 (DE) .......................... 10 2006 003 677
Oct. 12, 2006 (DE) .......................... 10 2006 048 300

(51) Int. Cl.
C07D 207/08    (2006.01)
A61K 31/40    (2006.01)
G01N 33/86    (2006.01)
(52) U.S. Cl. ........................... 548/571; 514/428; 436/69
(58) Field of Classification Search ........................ None
See application file for complete search history.

(56) References Cited

U.S. PATENT DOCUMENTS

| 5,633,381 | A | 5/1997 | Dallas et al. |
| 2005/0070479 | A1 | 3/2005 | Steinmetzer et al. |
| 2006/0148901 | A1 | 7/2006 | Stüerzebecher et al. |
| 2007/0066539 | A1 | 3/2007 | Stüerzebecher et al. |

FOREIGN PATENT DOCUMENTS

| EP | 1 217 000 A1 | 6/2002 |
| WO | WO 97/24118 A1 | 7/1997 |
| WO | WO 98/49563 A1 | 11/1998 |
| WO | WO 02/46159 A1 | 6/2002 |
| WO | WO 02/059065 A2 | 8/2002 |
| WO | WO 03/076457 A1 | 9/2003 |
| WO | WO 2004/062657 A1 | 7/2004 |
| WO | WO 2005/026198 A1 | 3/2005 |

OTHER PUBLICATIONS

Batt, D.G., et al., "5-Amidinoindoles as dual inhibitors of coagulation factors IXa and Xa," *Bioorg. Med. Chem. Lett.* 14(21): 5269-73, Elsevier Science Ltd., England (2004).
Choi-Sledeski, Y.M., et al., "Discovery of an Orally Efficacious Inhibitor of Coagulation Factor Xa Which Incorporates a Neutral $P_1$ Ligand," *J. Med. Chem.* 46(5): 681-684, American Chemical Society, United States (2003).
Deng, J.Z., et al., "Benzoxazole Thrombin and Factor Xa Inhibitors," 226th ACS National Meeting, *MEDI* 80, New York City, Sep. 7-11, 2003.
Dixon, M., "The determination of enzyme inhibitor constants," *Biochem. J.* 55(1): 170-1, Published by Portland Press on behalf of the Biochemical Society, England (1953).
Guertin, K.R., et al., "Optimization of the β-aminoester class of factor Xa inhibitors. Part 2: Identification of FXV673 as a potent and selective inhibitor with excellent In vivo anticoagulant activity," *Bioorg. Med. Chem. Lett.* 12(12): 1671-4, Elsevier Science Ltd., England (2002).
Hinder, M. et al., "Anticoagulant and anti-platelet effects are maintained following coadministration of otamizaban, direct factor Xa inhibitor, with tirofiban in healthy volunteers," *Thromb. Haemost.* 93(4): 794-5, Schattauer, Germany (2005).
Hirayama, F., et al., "Design, synthesis and biological activity of YM-60828 derivatives. Part 2: potent and orally-bioavailable factor Xa inhibitors based on benzothiadiazine-4-one template," *Bioorg. Med. Chem.* 11(3): 367-81, Elsevier Science, England (2003).
Jia, Z.J., et al., "1-(2-Naphthyl)-1H-pyrazole-5-carboxylamides as potent factor Xa inhibitors. Part 3: Design, synthesis and SAR of orally bioavailable benzamidine-P4 inhibitors," *Bioorg. Med. Chem. Lett.* 14(5): 1229-34, Elsevier Science Ltd., England (2004).
Katakura, S., et al., "A novel factor Xa inhibitor: structure-activity relationships and selectivity between factor Xa and thrombin," *Biochem. Biophys. Res. Commun.* 197(2): 965-72, Academic Press, United States (1993).
Maignan, S. and Mikol, V., "The use of 3D structural data in the design of specific factor Xa inhibitors," *Curr. Top. Med. Chem.* 1(2): 161-74, Bentham Science Publishers, Netherlands (2001).
Mederski, W.W., et al., "Chlorothiophenecarboxamides as P1 surrogates of inhibitors of blood coagulation factor Xa," *Bioorg. Med. Chem. Lett.* 14(23): 5817-22, Elsevier Science Ltd., England (2004).
Mederski, W.W., et al., "Halothiophene benzimidazoles as P1 surrogates of inhibitors of blood coagulation factor Xa," *Bioorg. Med. Chem. Lett.* 14(14): 3763-9, Elsevier Science Ltd., England (2004).
Nowak, G., et al., "Platelet adhesion assay—a new quantitative whole blood test to measure platelet function," *Semin. Thromb. Hemost.* 31(4): 470-5, Thieme, United States (2005).
Pauls, H.W., et al., "The Design of Competitive, Small-molecule Inhibitors of Coagulation Factor Xa," *Frontiers in Medicinal Chemistry—Online* 1(1): 129-152, Bentham Science Publishers Ltd., Netherlands (2004).
Perzborn, E., et al., "In vitro and in vivo studies of the novel antithrombotic agent BAY 59/7939—an oral, direct Factor Xa inhibitor," *J. Thromb. Haemost.* 3(3): 514-21, Blackwell Publications, England (2005).

(Continued)

Primary Examiner — James D Anderson
(74) Attorney, Agent, or Firm — Sterne, Kessler, Goldstein & Fox PLLC

(57) ABSTRACT

The present invention relates to a method for the anticoagulation of human blood ex vivo in which blood calcium concentration remains the same, no thrombin is formed and thrombocyte function is not affected. The invention further relates to a blood coagulation factor Xa inhibitor that can be advantageously used in this method, an agent that contains an inhibitor of the blood coagulation factor Xa, and a kit for diagnosing cellular blood components. The anticoagulated blood obtained according to the invention can be used for examining cellular blood components, for example for the diagnosis of thrombocyte function.

11 Claims, 10 Drawing Sheets

OTHER PUBLICATIONS

Quan, M.L. & Smallheer, J.M., "The race to an orally active Factor Xa inhibitor: recent advances," *Curr. Opin. Drug Discov. Devel.* 7(4): 460-9, Thomson Reuters (Scientific) Ltd., England (2004).

Quan, M.L. & Wexler, R.R., "The design and synthesis of noncovalent factor Xa inhibitors," *Curr. Top. Med. Chem.* 1(2): 137-49, Bentham Science Publishers, Netherlands (2001).

Saiah, E. & Soares, C., "Small molecule Coagulation Cascade Inhibitors in the Clinic," *Curr. Top. Med. Chem.* 5(16): 1677-95, Bentham Science Publishers, Ltd., Netherlands (2005).

Schweinitz, A., et al., "Design of novel and selective inhibitors of urokinase-type plasminogen activator with improved pharmacokinetic properties for use as antimetastatic agents," *J. Biol. Chem.* 279(32): 33613-22, American Society for Biochemistry and Molecular Biology, United States (2004).

Schweinitz, A., et al., "New substrate analogue inhibitors of factor Xa containing 4-amidinobenzylamide as P1 residue: part 1," *Med. Chem.* 2(4): 349-61, Bentham Science Publishers, Ltd., Netherlands (2006).

Shaw, K.J., et al., "(Z,Z)-2,7-Bis(4-amidinobenzylidene)cycloheptan-1-one: identification of a highly active inhibitor of blood coagulation factor Xa," *J. Med. Chem.* 41(19): 3551-6, American Chemical Society, United States (1998).

Song, Y., et al., "Design and synthesis of factor Xa inhibitors and their prodrugs," *Bioorg. Med. Chem. Lett.* 13(2): 297-300, Elsevier Science Ltd., England (2003).

Song, Y., et al., "Substituted acrylamides as factor Xa inhibitors: improving bioavailability by P1 modification," *Bioorg. Med. Chem. Lett.* 12(15): 2043-6, Elsevier Science Ltd., England (2002).

Stürzebecher, J., et al., "Synthetic inhibitors of bovine factor Xa and thrombin comparison of their anticoagulant efficiency," *Thromb. Res.* 54(3): 245-252, Pergamon Press, United States (1989).

Walsmann, P., "On the purification of thrombin preparations," *Pharmazie 23*: 401-402, Govi-Verlag Pharmazautischer Verlag, Germany (1968).

Willardsen, J.A., et al., "Design, synthesis, and biological activity of potent and selective inhibitors of blood coagulation factor Xa," *J. Med. Chem.* 47(16): 4089-99, American Chemical Society, United States (2004).

Zhang, P., et al., "Design, synthesis, and SAR of anthranilamide-based factor Xa inhibitors with improved functional activity," *Bioorg. Med. Chem. Lett.* 14(4): 989-93, Elsevier Science Ltd., England (2004).

International Search Report for International Application No. PCT/EP2007/000661, mailed Jul. 26, 2007, 14 pages, European Patent Office, Rijswijk, Netherlands.

International Preliminary Report on Patentability for International Application No. PCT/EP2007/000661, issued on Oct. 14, 2008, 15 pages, European Patent Office, Geneva, Switzerland.

ANTICOAGULATION OF HUMAN BLOOD EX VIVO

This application is a 35 U.S.C. §371 U.S. National Phase filing of International Application No. PCT/EP2007/000661, filed Jan. 26, 2007, which claims the benefit of German Patent Application No. 10 2006 003 677.8, filed Jan. 26, 2006, and German Patent Application No. 10 2006 048 300.6, filed Oct. 12, 2006. Each application is incorporated by reference herein in its entirety.

The present invention relates generally to a method for the anticoagulation of human blood ex vivo and to the use of the anticoagulated blood for the diagnosis of cellular blood components such as thrombocytes, for example. The invention further relates to a kit for diagnosing of cellular blood components. The present invention further relates to an inhibitor of the blood coagulation factor Xa and the use of this inhibitor for the anticoagulation of human blood ex vivo. The invention also relates to a method for the anticoagulation of human blood ex vivo in which this inhibitor is used. The invention further relates to the use of the inhibitor of the blood coagulation factor Xa for the anticoagulation of human blood ex vivo for diagnostic purposes or for the preservation and storage of blood products such as thrombocyte apheresis concentrates. The present invention further relates to a tube containing this inhibitor for taking blood samples, an apheresis hose/bag system containing this inhibitor and a thrombocyte concentrate containing this inhibitor. This invention also relates to a kit for diagnosing cellular blood components such as thrombocytes, for example.

Day after day the human body suffers from hundreds of mostly minor, but sometimes also greater internal and external lesions. So that these lesions remain without serious consequences to health, the blood coagulation system ensures that in the event of a lesion a wound is closed and the blood congeals after leaving the blood vessel. This blood coagulation consists essentially of two components: the primary haemostasis due to the function of the thrombocytes, and the plasmatic coagulation, which requires the interaction of a multiplicity of blood coagulation factors. However, the blood coagulation system may be varied in many people due to acquired or congenital thrombocyte function disorders. This gives rise to risks of haemorrhage of varying degrees and may result spontaneously or perioperatively in acutely life-threatening blood coagulation disorders.

For this reason it is necessary, particularly before operative or invasive interventions, to examine the functional suitability of thrombocytes on blood samples deriving from the patient. However, the plasmatic coagulation of the blood (fibrin formation system) in this case causes extraordinarily serious sampling difficulties. This gives rise to a situation where the blood remains completely uncoagulated only for a short time after sampling, and rapid aggregation of the blood platelets (thrombocytes) is induced by the formation of thrombin. However, reliable thrombocyte function tests can no longer be carried out in a sample with activated or aggregated thrombocytes.

Blood coagulation is based on a cascade-like sequence of reactions. Here inactive pro-enzymes are converted proteolytically to active proteases which in turn activate the next pro-enzyme in the cascade. In principle, blood coagulation can take place in initially two different ways, intrinsically and extrinsically.

In the case of intrinsic coagulation blood coagulation factors XII, XI and IX are initially activated on the basis of the protease kallikrein. Blood coagulation factor Xa is then activated in a reaction that is dependent on the presence of calcium ions, anionic phospholipids and the activated blood coagulation factor VIIIa. Extrinsic coagulation results in the activated blood coagulation factor Xa on the basis of thromboplastin and blood coagulation factor VIIa. In the presence of calcium ions, anionic phospholipids and blood coagulation factor Va, factor Xa is capable of catalysing the formation of thrombin (blood coagulation factor IIa) from the pro-enzyme prothrombin. Finally, thrombin gives rise to the conversion of the soluble plasma protein fibrinogen to polymerisable fibrin, and this is deposited as a fibrous network in the primary thrombus.

However, thrombin is not only responsible for the formation of fibrin but also represents a strong activator of the thrombocytes. Here the thrombin formed in the blood coagulation cascade binds to the high affinity thrombin receptor of the thrombocytes, thereby finally inducing a shape change in the thrombocytes, followed by their aggregation and the release of procoagulatory components.

Several methods with which the prevention of coagulation, i.e. anticoagulation, can be achieved are known from the state of the art. In this case citrate or EDTA is used as standard. Because of the complexing of the calcium ions the activation of blood coagulation factors VII, IX, X and prothrombin is initially totally prevented so that the blood coagulates, i.e. neither fibrin is formed from fibrinogen, nor is an aggregation of the thrombocytes induced. After a time the anticoagulation is partially exhausted by activation of the coagulation system by means of the calcium-independent factors kallikrein, XII and XI so that traces of thrombin are eventually formed. Whilst the presence of citrate or EDTA has no direct influence on the different components of the coagulation system, the withdrawal of calcium ions has a negative effect on the cellular components found in the blood. Every living cell requires an intracellular calcium level to maintain their normal functionality. Because of the progressive withdrawal of calcium after the anticoagulation of blood by means of citrate or EDTA, there is an initial change in or limitation of the normal function of the cells, which may ultimately lead to the death of the cells. This applies particularly to the thrombocytes, but also applies to leukocytes and erythrocytes.

In the case of thrombocytes it is therefore very clear that diagnostic function tests in citrate- or EDTA-blood/plasma only produce reliable results for a few hours after blood sampling, and these results do not reflect the in vivo conditions where calcium ions are present.

Heparin and hirudin are used as alternative anticoagulants which do not act on the basis of calcium complexing. The inhibiting effect of heparin on the blood coagulation system is due to the binding on antithrombin III. Antithrombin III deactivates serin proteases such as thrombin and other blood coagulation factors such as XIIa, XIa, Xa and IXa irreversibly to a large extent. The interaction of antithrombin III with heparin results in an increase in the speed of these reactions due to antithrombin III and therefore effectively prevents coagulation. However, heparin has a high affinity with certain receptors required to activate thrombocytes, which means that blood treated with heparin cannot be used for thrombocyte function tests, for example.

Hirudin is a high affinity, natural inhibitor of the fibrinogen-splitting coagulation enzyme thrombin. A sufficient hirudin concentration is actually capable of keeping human bloods uncoagulated over a long period of time. However, since hirudin inhibits thrombin exclusively, and therefore suppresses fibrin formation, the coagulation cascade is increasingly activated until thrombin is formed. Although the thrombin formed is largely bound by the hirudin, some of the hirudin is nevertheless capable of binding the high-affinity thrombin receptor of the thrombocytes. This results in the activation of the thrombocytes by changing their shape, aggregating and releasing components. It has been shown that no improvement in diagnosis of the thrombocyte function is possible with an anticoagulation of the blood by hirudin.

Citrate full blood or platelet-rich plasma (PRP) from citrate full blood is used for the current methods of thrombocyte function diagnosis. Since thrombocytes require calcium ions for their normal function, the results of the thrombocyte function tests in citrate full blood do not reflect the in vivo conditions. This fact stands very much in the way of a broader application of thrombocyte function tests. If clinically significant function tests were to be successfully carried out reproducibly in the physiological environment, a screening test for thrombocyte function would be carried out before each operative or invasive intervention in order reliably to detect the frequent thrombocyte function disorders (thrombocytopathies). Furthermore, the implementation of suitable thrombocyte function tests for detecting a thrombocyte over-function as a risk factor for cardiac infarction and heart attack, and for monitoring a therapy with thrombocyte function inhibitors (e.g. aspirin, Clopidogrel, parenterally administered thrombocyte function inhibitors) are considerably facilitated.

The object of the invention is therefore to find a new method for the anticoagulation of human blood in which neither the calcium concentration in the blood is varied nor thrombin is formed, and where the function of the thrombocytes is not influenced, so that the blood so anticoagulated can be used for diagnosing cellular blood components such as thrombocytes, for example. A further object is to find a compound which enables this method to be successfully carried out.

It has now been found, surprisingly, that human blood remains uncoagulated over a longer period of time without the formation of thrombin and without influencing the thrombocyte function if the coagulation cascade is interrupted by an inhibitor of blood coagulation factor Xa. In a preferred embodiment this inhibitor has a compound according to formula (I),

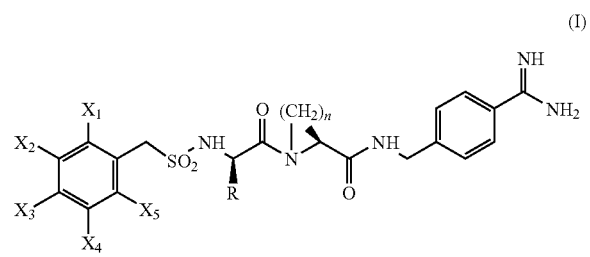

where n may be=2, 3 or 4, R=—$(CH_2)_m$—NH—Y, with m=1, 2, 3, 4 or 5, where Y may be=H or

and where $X_1, X_2, X_3, X_4, X_5$ may independently be H, F, Cl, Br, I, $NO_2$, $NH_2$, OH, alkyl or alkoxy.

According to the invention a method is made available with which the anticoagulation of human blood ex vivo can be achieved and which enables the anticoagulated blood to be used for diagnosing cellular blood components, e.g. for thrombocyte function tests. This method is characterised in that at least one agent with a direct inhibitory action on the blood coagulation factor Xa is added to the blood sampled. In a preferred embodiment this agent is a compound according to formula (I). The invention also relates to a tube for taking blood samples, an apheresis hose-bag system and a thrombocyte concentrate which contain this compound.

In the sense of the invention anticoagulation means that the re-formation of thrombin is inhibited in the sampled blood. According to the invention thrombin re-formation is inhibited when no more than 1 nM of thrombin is re-formed in the sampled blood. As described above, the activation of prothrombin to thrombin represents an essential step in the blood coagulation cascade. In this case the prothrombin fragment 1+2 (F1+2) is released in equivalent quantities. It is therefore possible to quantify the thrombin actually formed by determining the fragment produced, thus enabling the prothrombin fragment F1+2 to be used as an indirect marker of an activation of prothrombin to thrombin. The concentration of the prothrombin fragment F1+2 formed may be determined immunologically, for example, with commercial enzyme immunoassays (for example Enzygnost F1+2 micro, Dade Behring GmbH, Marburg).

According to the invention anticoagulation therefore means that no more than 1 nM of prothrombin fragment F1+2 is newly formed in the blood after its sampling. For example, if the initial concentration of the prothrombin fragment F1+2 in the blood sample immediately after blood sampling is 0.3 nM, the blood present in the sample is anticoagulated, within the meaning of the invention, until the total concentration of the prothrombin fragment F1+2 in the blood does not exceed 1.3 nM in this example. Without suitable treatment of the blood to prevent coagulation there is an increase in the concentration of the prothrombin fragment F1+2 in this example to well over 1.3 nM, within a few minutes, due to the plasmatic coagulation, i.e. the blood coagulates. As a result of the inventive method the concentration of the prothrombin fragment F1+2 does not exceed 1.3 nM in this example over a long period of time (48 hours, for example), i.e. the blood is anticoagulated during this period.

The period during which the anticoagulation of human blood ex vivo can be maintained using the method according to the invention, i.e. the period of time from sampling of the blood to the time at which more than 1 nM of thrombin has been newly formed, is over 8 hours, preferably over 12 hours and even more preferably over 24 hours.

Finally, due to the inhibition of the thrombin formation, the activation of the thrombocytes induced by thrombin is also largely prevented. When the thrombocytes are activated thrombocyte components (e.g. platelet factor 4 (PF 4), beta-thromboglobulin, serotonin, ADP/ATP and microparticles) are released from the thrombocyte granula into the plasma and activation markers are expressed on the thrombocyte surface (e.g. P-selection, thrombospondin, multimerin, DC63, LAMP-1, PAC1 or 9F9). The inhibition of the activation of the thrombocytes by inhibition of thrombin formation can be demonstrated by measuring the concentration of these thrombocyte components or activation markers (e.g. by means of test kits, for example PF4: ELISA PF4, Haemochrom Diagnostica GmbH, Essen).

The term "blood" used here includes not only full blood, but also generally blood capable of coagulation in pure, diluted or concentrated form, where the blood may have its natural composition or may even deviate from it. The term blood may therefore also include, for example, platelet-rich plasma (PRP) or other blood products such as thrombocyte concentrates or thrombocyte apheresis concentrates.

The human blood used for the method according to the present invention may be sampled by any method known to the person skilled in the art. The blood sample is preferably taken by venous puncture.

When used according to the invention, "ex vivo" refers to processes that take place outside the human or animal organism. In the sense of the invention "ex vivo" also has the meaning of "in vitro". Thus "ex vivo" refers both to tests on samples where there is still a link between the sample and the human being or animal and to tests in which this link no longer exists. Processes which take place within the human or animal body are expressly excluded from the term ex vivo.

According to the invention the anticoagulation of human blood ex vivo is achieved when at least one agent with a direct inhibitory action on the blood coagulation factor Xa is added to the sampled blood.

Here direct inhibitory action means that there is a direct interaction between the inhibitor on the one hand and the molecule to be inhibited on the other. On the contrary, the inhibiting action of an indirect inhibitor, for example, is due to the fact that it binds to a direct inhibitor and reinforces this inhibiting action. Heparin, for example, is therefore an indirect inhibitor of blood coagulation factors since it binds antithrombin III and potentiates its inhibitory activity, but does not interact directly with the coagulation factors to be inhibited. Another example of an indirect inhibitor is one which does not bind the molecule to be inhibited itself but interacts with a cofactor of this molecule, thereby preventing its function.

Direct inhibitors of the blood coagulation factor Xa are therefore inhibitors which enter into direct interaction with the blood coagulation factor Xa, thereby deactivating it. An inhibitor which inhibits an enzyme or a plurality of enzymes which precede the blood coagulation factor in the blood coagulation cascade, such as the blood coagulation factors XIIa, XIa, IXa or VIIa, for example, but does not interact with the blood coagulation factor Xa in order to inhibit its function in the blood coagulation cascade, is therefore an indirect inhibitor of the blood coagulation factor Xa. On the other hand, a direct inhibitor of the blood coagulation factor Xa may also be an inhibitor which directly inhibits the blood coagulation factor Xa and also inhibits further enzymes that precede the blood coagulation factor Sa in the blood coagulation cascade, for example.

According to the invention it is essential for the at least one agent to exert a direct inhibitory action on the blood coagulation factor Xa whilst at the same time not impairing the activatability of the thrombocytes. The precise structural condition of the agent is insignificant here as long as it meets these requirements.

According to the state of the art there are a multiplicity of direct inhibitors of the blood coagulation factor Xa which can be used as an agent in this invention (Overview article: Quan and Smallheer, Curr. Opin. In Drug Discovery & Development 7, 460, 2004; Pauls et al., Frontiers in Medicinal Chemistry—Online 1, 129, 2004; Maignan and Mikol, Curr. Topics in Med. Chemistry 1, 161, 2001). Although these cannot be limited to a small number of substance classes, some of them can be assigned to certain substance classes. These substance classes include, for example, benzamidine derivatives (Song et al., Bioorg. Med. Chem. Lett. 13, 297, 2003), bis-benzamidines, benzylamine derivatives, aminobenzisoxazol derivatives, naphthamidine derivatives, ketopiperazine derivatives, 5-chlorothiophen derivatives, various compounds with bicyclic nuclei, triazol derivatives (Deng et al. 226$^{th}$ ACS National Meeting New York, USA, MEDI 80, 2003), chlorindol derivatives (Sheehan et al., Bioorg. Med. Chem. Lett. 12, 2043, 2002), chloronaphthyl derivatives (Jia et al., Bioorg. Med. Chem. Lett. 14, 1229, 2004), chloropyridyl derivatives (Zhang et al., Bioorg. Med. Chem. Lett. 14, 989, 2004), 1-aminoisochinoline derivatives (Song et al., Bioorg. Med. Chem. Lett. 14, 1229, 2004) or benzoxazinone derivatives.

Examples of inventive inhibitors include BABCH (Pefabloc tPA/Xa; Stürzebecher et al., Thromb. Res. 54, 245, 1989), ZK 807834 (Berlex Biosciences, Shaw et al., J. Med. Chem. 41, 3551, 1998), FXV 673 (Otamixaban, Sanofi-Aventis; Guertin et al., Bioorg. Med. Chem. Lett. 12, 1671, 2002), DPC 423 and DPC 602 (each from Bristol-Myers-Squibb; Quan and Wexler, Curr. Topics Med. Chem. 1, 137, 2001), DPC 906 (Razaxaban; Batt et al., Bioorg. Med. Chem. Lett. 14, 5269, 2004), DX-9065a (Daiichi; Katakura et al., Biochem. Biophys. Res. Chem. 197, 965, 1993), YM-60828 (Yamanouchi Pharmaceutical Co.; Hirayama et al., Bioorg. Med. Chem. 11, 367, 2003), RPR 209685 (Sanofi-Aventis; Choi-Sledeski et al., J. Med. Chem. 46, 68, 2003), BAY 59-7939 (Bayer; Perzborn et al., J. Thromb. Haemost. 3, 514, 2005), EMD 495235 (Merck Darmstadt; Mederski et al., Bioorg. Med. Chem. Lett. 14, 3763, 2004; Mederski et al., Bioorg. Med. Chem. Lett. 14, 5817, 2004), PD-198961 (Pfizer; Willardsen et al., J. Med. Chem. 47, 4089, 2004), Pefabloc tPA/Xa (Pentapharm Ltd. Basel, Switzerland) and CJ-FXa (Haemochrom Diagnostica GmbH, Essen). Otamixaban (2-(R)-(3-carbaminidoyl benzyl)-3-(R)-[4-(1-oxy-pyridin-4-yl)benzoylamino]butyric acid methyl ester), Pefabloc tPA/Xa (2,7-bis(4-amidinobenzylidene)-cycloheptanone-(1); Pentapharm Ltd. Basel, Switzerland) and CJ-FXa (benzylsulphonyl-D-arginyl-glycyl-4-amidinobenzylamide) have been shown to be preferred inhibitors. Otamixaban has proved to be a particularly preferred inhibitor.

A further particularly preferred inhibitor is a compound according to formula (I)

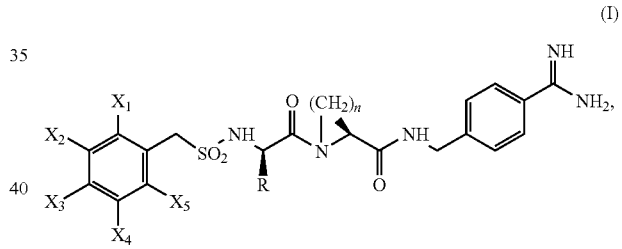

where n may be=2, 3 or 4, R=—$(CH_2)_m$—NH—Y, with m=1, 2, 3, 4 or 5, where Y may be=H or

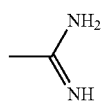

and where $X_1$, $X_2$, $X_3$, $X_4$, $X_5$ may independently be H, F, Cl, Br, I, $NO_2$, $NH_2$, OH, allkyl or alkoxy.

A further inhibitor particularly preferred for the inventive method is an inhibitor according to formula (I), where n is=3 or 4, R=—$(CH_2)_m$—NH—Y, with m=2, 3 or 4, where Y is=H or

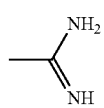

and where $X_1$, $X_2$, $X_3$, $X_4$, $X_5$ are independently H, F, Cl, Br, I, $NO_2$, $NH_2$, OH, alkyl or alkoxy.

According to a further preferred embodiment of the present invention the inhibitor of the blood coagulation factor Xa is a compound according to formula (I), where n is=3, R=—(CH$_2$)$_m$—NH—Y, with m=3, where Y is=or

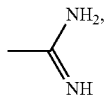

and where X$_1$, X$_2$, X$_3$, X$_4$, X$_5$ are each H. This compound has the structure according to formula (II).

(II)

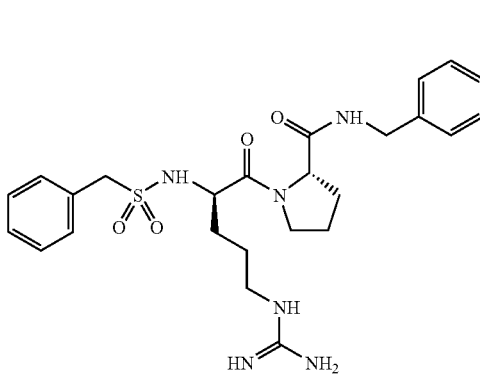

and is also referred to in the following as benzylsulphonyl-D-arginyl-prolyl-4-amidinobenzylamide or BAPA' for short.

According to another preferred embodiment of the present invention the inhibitor of the blood coagulation factor Xa is a compound according to formula (I), where n is =2, R=—(CH$_2$)$_m$—NH—Y, with m=3, where Y is=

and where X$_1$, X$_2$, X$_3$, X$_4$ and X$_5$ are each H.

In a further preferred embodiment of the invention the inhibitor of the blood coagulation factor Xa is a compound according to formula (I), where n=3, R=—(CH$_2$)$_m$—NH—Y, with m=4, where Y is=H, and where X$_1$, X$_2$, X$_3$, X$_4$ and X$_5$ are each H.

In a further preferred embodiment of the invention the inhibitor of the blood coagulation factor Xa is a compound according to formula (I), where n=3, R=—(CH$_2$)$_m$—NH—Y, with m=3, where Y is=

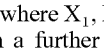

and where X$_1$, X$_2$, X$_3$, X$_4$ and X$_5$ are each H, and X$_3$=Cl.

The inhibitors of the blood coagulation factor Xa described herein may also be present in the form of salts, preferably physiologically acceptable salts. For example, the compounds may be present as salts with acids, e.g. mineral acids or suitable organic acids. The inventive inhibitors of the blood coagulation factor Xa are preferably present according to formula (I) as salts of trifluoroacetic acid (TFA).

Quite simply the preferred inventive inhibitor of the blood coagulation factor Xa according to formula (I) has the structure P$_4$—P$_3$—P$_2$—P$_1$ with the following four components:

P1: A 4-amidinobenzyl amine residue according to

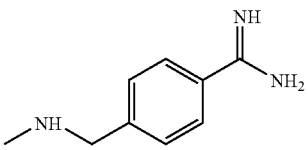

P2: A residue of a cyclic amino acid according to

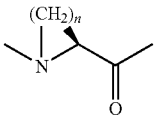

with n=2, 3 or 4;

P3: A residue of a basic amino acid according to

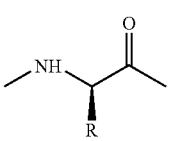

with R=—(CH$_2$)$_m$—NH—Y, where m is=1, 2, 3, 4 or 5, and Y=H or

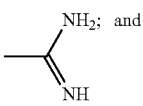

P4: A benzylsulphonyl residue which can be substituted singly or multiply on the benzol ring, according to

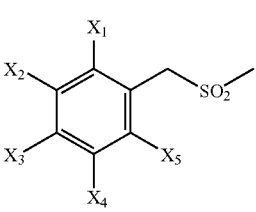

where X$_1$, X$_2$, X$_3$, X$_4$, X$_5$ may independently be H, F, Cl, Br, I, NO$_2$, NH$_2$, OH, alkyl or alkoxy.

The preferred inventive inhibitors of the blood coagulation factor Xa may be represented by the application or conversion of the method known to the person skilled in the art, the methods being understood to be those described in the literature, for example. For instance, the synthesis of the inventive inhibitors may be carried out on an analogy with the synthesis of benzylsulphonyl-D-arg-gly-4-amidinobenzylamide described in the literature (Schweinitz et al., Medicinal Chemistry 2, 349-361, 2006). For this purpose the two blocks corresponding to P4-P3-OH and H—P2-P1 are initially synthesised. The synthesis of the block P4-P3-OH, for example benzylsulphonyl-D-arg(Pbf)-OH may be carried out according to Schweinitz et al. (Medicinal Chemistry 2, 349-361, 2006). The block H—P2-P1, for example H-Pro-4-amidinobenzylamide×2HCl, can be synthesised according to Steinmetzer and Nowak (WO 02/059065). In this case the respective H—P2-4-amidinobenzylamide derivative is manufactured by catalytic hydration (with Pd/C) from the corresponding Cbz-P2-4-acetyl hydroxyamidinobenzylamide, which can be obtained by coupling the Cbz (carbobenzyloxy)-protected P2-amino acid and H-4-acetyl hydroxyamidobenzylamine.

The blocks may be coupled, for example, by means of HBTU (2-(1H-benzotriazol-1-yl)-1,1,3,3-tetramethyluronium hexafluorophosphate) or PyBop (benzotriazol-1-yl oxytripyrrolidinophosphonium hexafluorophosphate) and diisopropylethylamine in DMF (in the case of Arg in P3), followed by separation of the Pbf protective group by means of trifluoroacetic acid). It is clear to the person skilled in the art that the inventive inhibitors of the blood coagulation factor Xa can obviously also be synthesised by a method other than that described above, for example using a P2-P1-component in which the amidino group is present as acetylhydroxyamidine or as Cbz-protected amidine (Schweinitz et al., J. Biol. Chem. 279, 33613-33622, 2004).

In a preferred embodiment of the inventive method the direct inhibition of the blood coagulation factor Xa takes place competitively, the competitive inhibitor forming a stoichiometric reversible complex with the blood coagulation factor to be inhibited. This is also the case, for example, with the inventive inhibitors according to formula (I).

In a further preferred embodiment the agent with direct inhibitory action on the blood coagulation factor Xa is a synthetic molecule with a molecular weight <1000.

It is particularly advantageous for the inventive inhibitors of the blood coagulation factor Xa to have a strong inhibitory action on the blood coagulation factor Xa. Inhibitors of the blood coagulation factor Xa that have a direct inhibitory action on the blood coagulation factor Xa with $K_i$<10 nM, preferably <5 nM, in particular <3 nM, are particularly advantageous to the inventive method, $K_i$ standing for the dissociation constant of the enzyme-inhibitor complex, i.e. for the quotient of the product of the concentrations of the enzyme and inhibitor and the concentration of the enzyme-inhibitor complex. Strong inhibitors therefore form stable enzyme-inhibitor complexes and result in lower $K_i$ values than is the case with weaker inhibitors. The $K_i$ value is preferably determined by measuring the enzyme activity at least two substrate concentrations and at least three different inhibitor concentrations. The method of determining the $K_i$ values is implemented at 25° C. in tris-buffer (0.05 mol/l, pH 8.0, containing 0.154 mol/l NaCl and 5% ethanol). For this purpose 200 µl of inhibitor solution (dissolved in the above-mentioned tris-buffer) are mixed with 25 µl of substrate ($CH_3OCO$-D-cha-gly-arg-pNA; with Cha=cyclohexylamine and pNA=para-nitroaniline; sold by Pentapharm AG, Basel, Switzerland under the commercial name of Pefachrome FXa; dissolved in $H_2O$), and the reaction is started by the addition of 50 µl of enzyme (blood coagulation factor Xa, for example from Haemochrom Diagnostica GmbH, Essen; dissolved in 0.154 mol/l NaCl). After a reaction time of 3-5 minutes acetic acid (25 µl) is added and the extinction of the solution is measured at 405 nm with a Microplate reader (for example iEMS Reader MF 1401, Labsystems, Helsinki, Finland). The evaluation is carried out graphically according to Dixon's method (Biochem J. 55, 170, 1953).

In an even more preferred embodiment the direct inhibitor of the blood coagulation factor Xa acting as an agent in this invention inhibits at least one further enzyme in the early phase of the blood coagulation, for example plasma kallikrein and/or the blood coagulation factors XIa, XIIa and/or VIIa. This may already influence the incipient blood coagulation activation at an early stage.

The inventive compounds according to formula (I) are surprisingly capable of inhibiting at least one further enzyme of the blood coagulation, particularly thrombin, in addition to the blood coagulation factor Xa. In a particularly preferred embodiment the compound according to Formula (I) inhibits not only the blood coagulation factor XA but also thrombin and/or plasma kallikrein. In a quite particularly preferred embodiment the inventive inhibitor of the blood coagulation factor Xa according to formula (I) has an inhibitory action on thrombin with $K_i$<10 nM, preferably <5 nM, and quite preferably <3 nM, or on plasma kallikrein with $K_i$<20 nM, preferably <10 nM, and quite preferably <5 nM. Here too the $K_i$ value stands for the dissociation constant of the respective enzyme-inhibitor complex. The determination of the $K_i$ values of the inhibitors vis-a-vis thrombin and plasma kallikrein is preferably carried out in a similar manner to the determination, described above, of the $K_i$ values of the inhibitors vis-a-vis the coagulation factor Xa, but in this case $CH_3SO_2$-D-HHT-gly-arg-pNA (with HHT=hexahydrothyrosin, and pNA=para-nitroaniline; sold under the commercial name Pefachrome tPA) are used as substrates in the case of thrombin and bz-pro-phe-arg-pNA (with bz=benzyl-, and pNA=para-nitroaniline; sold under the commercial name Chromozym PK) in the case of plasma-kallikrein.

Furthermore it may be preferable to use not only one, but a plurality of different inhibitors with variably specific inhibitor action on the blood coagulation factor Xa and, if necessary, on further blood coagulation factors for the method according to the invention. This gives rise, for example, to a combined inhibitory action which reinforces the action of the inventive method. For example, the inventive method may also be implemented by adding to the blood, in addition to a certain inhibitor of the coagulation factor Xa according to formula (I), a further inhibitor of the blood coagulation factor Xa according to formula (I) and/or another inhibitor of the blood coagulation factor Xa or another blood coagulation factor preceding the blood coagulation factor Xa in the blood coagulation cascade.

It should be expressly noted at this point that the anticoagulation of human blood ex vivo can also be achieved if at least one agent with direct inhibitory action on a blood coagulation factor other than Xa is added to the sampled blood. Thus human blood ex vivo can also be anticoagulated according to the invention if no direct inhibitor of the blood coagulation Xa, but at least one inhibitor of other blood coagulation factors preceding the blood coagulation factor Xa in the blood coagulation cascade (for example, plasma-kallikrein) is added to it. However, these inhibitors generally result in success only in relatively high concentrations, and in most cases only when the affinity of the inhibitor to the blood coagulation factor to be inhibited is very high. It has been shown that although the inhibition of the blood coagulation factor Xa is not the only indication of effective anticoagulation of human blood ex vivo, it is by far the most preferable to the inhibition of other blood coagulation factors. Although this invention will not be limited by the basic mechanism, the phenomena described above may be due to the fact that both the intrinsic and extrinsic method of blood coagulation lead to the activated blood coagulation factor Xa. The activity of the blood coagulation factor Xa is essential for the formation and activation of thrombin, thus its inhibition results in anticoagulation. However, if it is not the blood coagulation factor Xa that is inhibited but, for example, an intrinsically active blood coagulation factor then, for example, thrombin can still be formed and activated by activating the extrinsic method. One reason for the particularly advantageous action that is achieved with the inhibitor of the blood coagulation factor Xa according to formula (I) is that this factor exerts a strong inhibitory action not only on the blood coagulation factor Xa but also on further blood coagulation factors such as thrombin and plasma-kalliekrein for example.

It is clear to the person skilled in the art that the optimum concentration of the inhibitor or inhibitors to be used for the inventive method for the anticoagulation of human blood ex vivo varies. It is dependent on factors known to the person skilled in the art, such as the inhibiting strength and inhibiting specificity of the inhibitor, for example. However, if is not a problem, nor does it require any major expenditure, to determine the optimum concentration of the direct inhibitor of the blood coagulation factor Xa for the anticoagulation of human blood ex vivo. This can be done, for example, by mixing blood samples with different quantities of the inhibitor, thereby adjusting different concentrations of the inhibitor in the blood samples. The quantity of the prothrombin fragment 1+2 (F 1+2) in the samples can then easily be determined at the desired times using, for example, one of the commercially available immunological test kits in order to assess whether the formation of thrombin has been inhibited, i.e. whether anticoagulation has taken place according to the invention. The optimum concentration of the inhibitor can be determined in this way, easily and quickly, for the inventive method.

For the method according to the present invention the inventive inhibitor of the blood coagulation factor Xa may, for example, be present dissolved in a suitable solvent. A suitable solvent preferably has a physiological ionic strength and/or a physiological pH value. Examples of this are physiological salt solutions, e.g. NaCl solutions, or buffers. Furthermore, the inhibitor of the blood coagulation factor Xa according to formula (I) may also be present mixed with a preservative known to the person skilled in the art.

The anticoagulation is preferably achieved by the inventive method by mixing 9 parts of blood and 1 part of a solution containing the inventive inhibitor.

For practical reasons it is often advantageous for the inventive inhibitor to be present directly in a tube for taking blood samples. The tube may, for example, be a commercially available blood sampling tube known from the state of the art. Exemplary blood sampling tubes comprise Monovettes (Sarstedt AG & Co., Nürnbrecht, Germany), Vacutainer systems (e.g. from Becton-Dickinson, Heidelberg, Germany) and modified designs thereof.

The inventive inhibitor or inventive inhibitors are preferably presented in such a quantity or in such a volume that the concentration of the inhibitor or inhibitors is sufficiently high, after the tube is filled with blood, to prevent the coagulation of blood according to the invention. This enables the medical specialist staff to achieve anticoagulation of human blood ex vivo without expensive working steps.

In a preferred embodiment the inventive method for the anticoagulation of human blood ex vivo is used for the preservation and storage of blood. The blood to be preserved and stored generally consists of blood products such as thrombocyte concentrates or thrombocyte apheresis concentrates.

The respective blood products are manufactured by the method known to the person skilled in the art.

Thrombocyte concentrates may, for example, be obtained from platelet-rich plasma (PRP) by centrifuging at high speed, the buffy coat (BC) of blood preserves containing thrombocytes or from thrombocyte apheresis concentrates of individual donors.

Thrombocyte apheresis concentrates may, for example, be obtained using a commercially available cell separator by means of thrombocyte apheresis.

In these cases it is often preferable, for example, for the inventive inhibitor for the anticoagulation of human blood ex vivo to be present directly in a blood bag known from the state of the art in a quantity that is effective for the inventive method. In particular preference the inventive inhibitor is present in a collection bag for receiving blood. In particular, it is preferable for this collection bag to be part of an apheresis hose/bag system known to the person skilled in the art. This apheresis hose/bag system may have both one or a plurality of collection bags which contain the inventive inhibitor. The inventive inhibitor may, for example, be present both in a bag in which the full blood taken from the donor is introduced, and in a bag in which the concentrates are finally collected.

In a preferred embodiment the inventive inhibitor for anticoagulation of human blood ex vivo is to be present in a sterile collection bag for infusion containing a thrombocyte concentrate.

According to a further embodiment of the invention the inventive inhibitor of the blood coagulation factor Xa may be used for isolating the cellular components of the blood.

In a further preferred embodiment the inventive method for anticoagulation of human blood ex vivo is preferably used for diagnostic purposes. For example, the agent with direct inhibitory action on the blood coagulation Xa or the blood anticoagulated with the agent according to the invention may be used for diagnosing cellular blood components.

The term "diagnosing cellular blood components" or synonyms thereof relate in particular, according to the invention, to tests which enable the medical specialist to make statements immediately on the nature, number, size, condition and functional suitability (for example activity and activatability) of cellular blood components.

The term cellular blood components will here cover, for example, thrombocytes, erythrocytes, reticulocytes and other erythrocytary preliminary stages known to the person skilled in the art, as well as leukocytes such as granulocytes, lymphocytes, monocytes, peripheral stem cells and other leukocytary preliminary stages known to the person skilled in the art, for example.

The methods for diagnosing cellular blood are well known to the person skilled in the art, examples being methods for assessing the thrombocyte functions, counting (for example, microscopic counting), morphological characterisation (for example on coloured and uncoloured blood smears) and typification of cells in the blood, preferably using microscopic, cytometric or flow cytometric methods, electronic particle counting, methods for detecting in vivo activation of haemostasis and fibrinolysis, quantification of markers of the activated thrombocytes, e.g. platelet factor 4 (PF 4), β-thromboglobulin, serotonin, ADP/ATP, prothrombin fragment F1+2, thrombin-antithrombin complexes, D-dimers, fibrinogen cleavage products, soluble fibrin or fibrin monomers, plasmin-plasmin inhibitor complexes, tPA-PAI complexes, or the electronically and cytochemically (e.g. peroxidase) aided morphological characterisation and counting of peripheral leukocytes and other cells in the blood, for example. The cellular components can be diagnosed by means of flow cytometry, for example, by characterising components of cell surfaces with marked antibodies (for example fluorescence-marked monoclonal antibodies), and counting the cells so marked in the flow cytometer (e.g. by electronic counting).

The blood anticoagulated according to the inventive method may be used, for example, for all conventional methods for assessing the thrombocyte functions. Exemplar methods include spontaneous thrombocyte aggregation according to Breddin, induced thrombocyte aggregation according to Born, impedance full blood aggregometry, the secretion (release) of thrombocytary constituents (e.g. ADP/ATP, plate factor 4, β-thromboglobulin, serotonin), thrombocyte propagation (e.g. according to Breddin), thrombocyte adhesion, determination of thrombocyte surface proteins after activation (e.g. by flow cytometry), measurement of the "in vitro bleeding time", e.g. with the platelet function analyser 100 (PFA-100; Dade Behring), thrombelastography, coagulation retraction, the platelet reactivity index (e.g. according to Grotemeyer, Wu & Hoak) and the platelet adhesion assay (e.g. according to Nowak et al. Semin. Thromb. Hemost. 31, 470, 2005).

Instruments preferably used for measurement include the clot signature analyser (CSA), the cone and platelet analyser (IMPACT), flow cytometer, Ichor-Platelet Works, the laser platelet aggregometer (PA-200), the haemostasis analysis system, Hemostasus, Ultegra (RPFA), the thrombotic status analyser (TSA), the Haemodyne platelet analysis system, VerifyNow, Platelet-Stat, the Multiplate analyser and other instruments for impedance aggregometry, as well as various instruments for the turbidimetric determination of thrombocyte aggregation according to Born.

The invention therefore also comprises a method for diagnosing cellular blood components, in which sampled blood ex vivo is anticoagulated by adding to the blood at least one agent with a direct inhibitory action on the blood coagulation factor Xa, then examining the cellular components of the blood. In a preferred embodiment the method for diagnosing thrombocytes is used in which, for example, the thrombocyte function tests described above are carried out with the blood anticoagulated according to the invention.

A further preferred embodiment of the invention is a kit which comprises at least one inventive inhibitor of the blood coagulation factor Xa and a means for examining cellular blood components. The means for examining cellular blood components contained in the kit comprises, in particular, a unit suitable for diagnosing cellular blood components and, if necessary, adapted to a device for diagnosing cellular blood components (e.g. a measuring cell or cartridge). In a preferred embodiment the kit contains, as a means for examining cellular blood components, a means for thrombocyte function diagnosis. This means for thrombocyte function diagnosis may, for example, be a measuring cell, a cartridge or another unit which is adapted to conventional devices for measuring thrombocyte function and can be used for assessing thrombocyte function. In a preferred embodiment the kit comprises, as a means for thrombocyte function diagnosis, or as a further component of the kit, a thrombocyte activator. This activator may be present in solid form, dissolved or on a carrier acting as a means for thrombocyte function diagnosis. The carrier may, for example, be a measuring cell known to the person skilled in the art for measuring closure times or a further unit suitable for measuring thrombocyte activity, if necessary a unit adapted to a measuring device known from the state of the art. The activator itself may be a thrombocyte activator known to the person skilled in the art. ADP, arachidonic acid (AA), thrombospondin, TRAP (Thrombin Receptor Activating Protein), collagen or epinephrine are mentioned by way of example.

All the above-mentioned tests for measuring thrombocyte functions are currently carried out in platelet-rich citrate plasma or in citrate full blood. The inventive method for the anticoagulation of human blood ex vivo has the advantage over the state of the art in that although plasmatic coagulation (i.e. the formation of thrombin followed by the formation of fibrin by thrombin) is inhibited, the activatability of the thrombocytes is not inhibited by suitable inductors, e.g. ADP, collagen, arachidonic acid, thrombospondin, epinephrine or TRAP (Thrombin Receptor Activating Protein). On the other hand, traces of thrombin, which is also a strong thrombocyte activator, always develop in time in the citrate environment, or the thrombocytes lose their functionality due to calcium extraction. The inventive method for the anticoagulation of human blood ex vivo therefore has the essential advantage that the inventive inhibitor need neither be removed nor deactivated before carrying out tests for diagnosing cellular blood components, such as thrombocyte function tests, for example, since it does not influence the thrombocyte function itself.

The above-mentioned analysis methods are in principle substantially disrupted if, during or after blood sampling ex vivo or in vitro, additional activation of the thrombocytes takes place. Consequently values that are too high are falsely measured, leading to a false laboratory finding interpretation, namely a supposedly strong activation of the haemostasis in vivo. The aggregability of the thrombocytes is fully obtained by the inventive method for the anticoagulation of human blood ex vivo, and the formation of thrombin and fibrin and hence the activation of the thrombocytes are prevented so that the values measured with the blood anticoagulated according to the invention are most likely to reflect the in vivo conditions.

EXAMPLES

The present invention is illustrated in the following with reference to examples, but these should not be regarded as limiting.

In examples 1-5 commercially available inhibitors of the blood coagulation factor Xa are used as inhibitors.

In examples 6-11 an inhibitor of the blood coagulation factor Xa according to formula (I) was used as inhibitor. The compound according to formula (II), BAPA', was used as an example for this. However, it should be expressly noted at this point that the inventive inhibitors are characterised by an extremely similar inhibitor spectrum. The inhibitors of the blood coagulation factor Xa according to formula (I) inhibit not only the blood coagulation factor Xa but other similar blood coagulation factors. Moreover, the $K_i$ values of the individual inventive inhibitors only differ from these further blood coagulation factors to a minimal degree, if at all. However, these possible deviations by no means impair the capability of the compounds according to formula (I) to inhibit the coagulation of human blood ex vivo successfully in the inventive method.

FIG. 1 shows the influence of Pefabloc tPA/Xa, an inhibitor of the blood coagulation factor Xa, on the formation of thrombin after activation with kaolin in plasma anticoagulated with hirudin. In the legend control −A means: hirudin-anticoagulated plasma without activation by kaolin addition, control +A means: hidurin-anticoagulated plasma plus kaolin, and the numerical values mean: hirudin-anticoagulated plasma mixed with kaolin plus Pefabloc tPA/Xa in the concentrations indicated.

FIG. 2 shows the influence of CJ-PK (benzylsulphonyl-D-seryl-carbobenzoxylsyl-4-amidinobezylamide, Haemochrom GmbH, Essen), an inhibitor of plasma-kallikrein, on the formation of thrombin after activation with kaolin in plasma anticoagulated with hirudin. In the legend control −A means: hirudin-anticoagulated plasma without activation by kaolin addition, control +A means: hidurin-anticoagulated plasma plus kaolin, and the numerical values mean: hirudin-anticoagulated plasma mixed with kaolin plus CJ-PK in the concentrations indicated.

FIG. 3 shows the influence of Otamixaban, an inhibitor of the blood coagulation factor Xa, on the formation of thrombin after activation with kaolin in plasma anticoagulated with hirudin. In the legend control −A means: hirudin-anticoagulated plasma without activation by kaolin addition, control +A means: hidurin-anticoagulated plasma mixed with kaolin, and the numerical values mean: hirudin-anticoagulated plasma plus kaolin and Otamixaban in the concentrations indicated.

Figure 6:
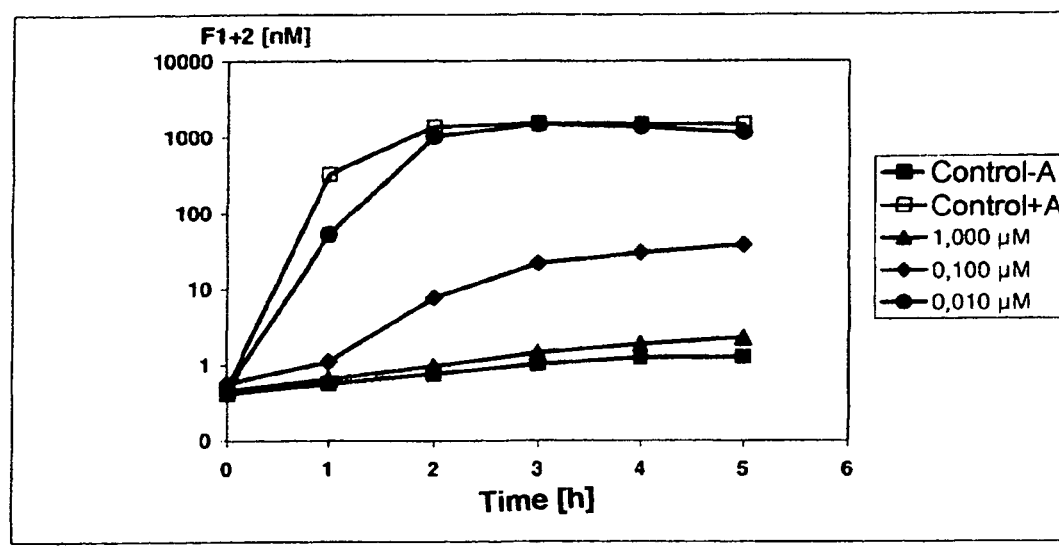

FIG. 6 shows the influence of BAPA' on the formation of thrombin after activation with kaolin in plasma anticoagulated with hirudin. In the legend control −A means: hirudin-anticoagulated plasma without activation by kaolin addition, control +A means: hidurin-anticoagulated plasma plus kaolin, and the numerical values mean: hirudin-anticoagulated plasma mixed with kaolin plus BAPA' in the concentrations indicated.

Figure 7:
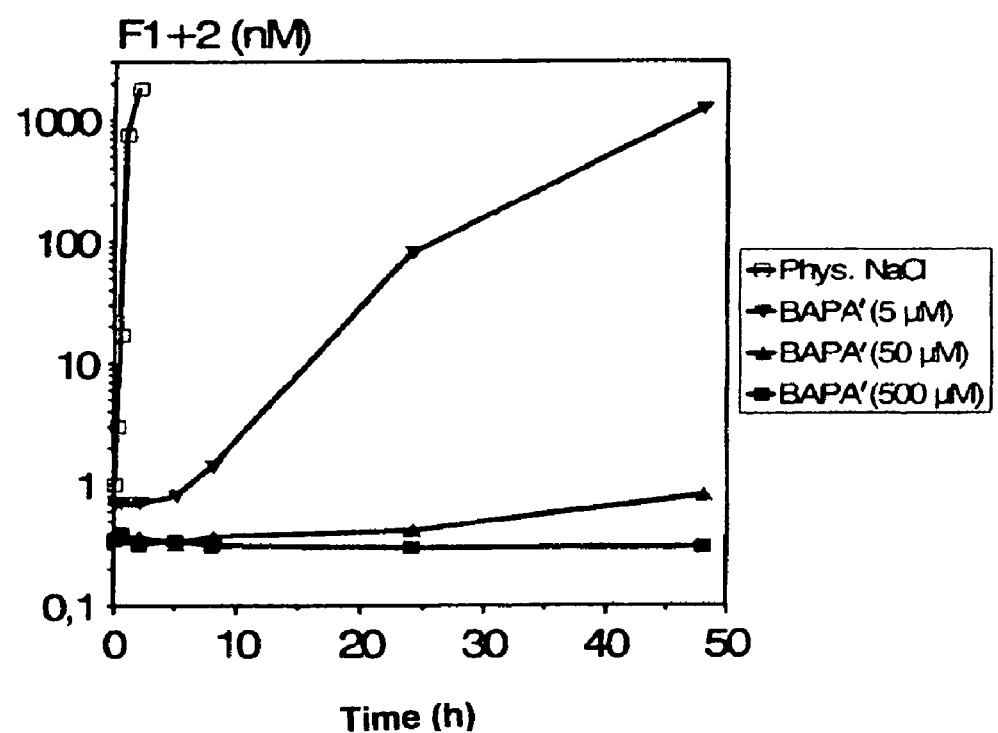
Figure 8A:
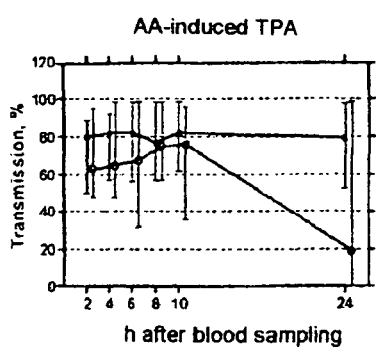
Figure 8B:
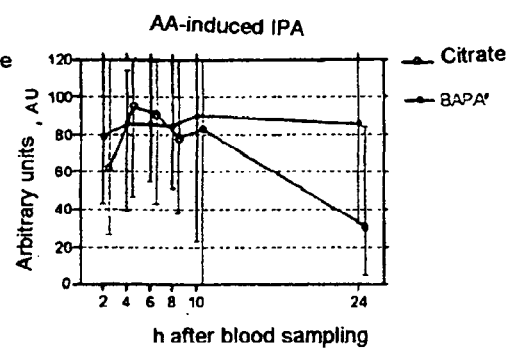
Figure 8C:
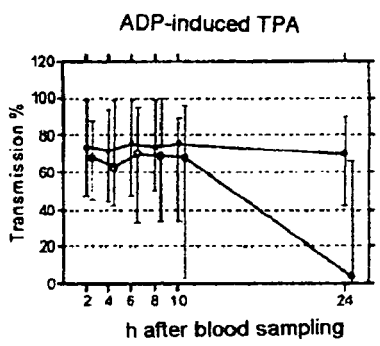
Figure 8D:
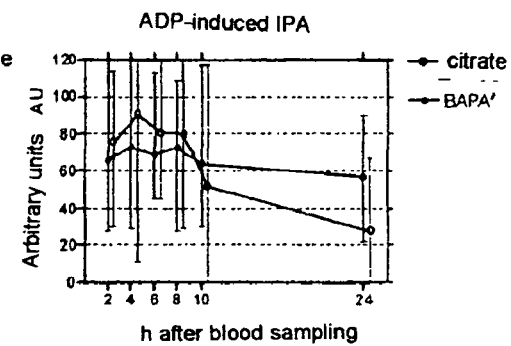
Figure 8E:
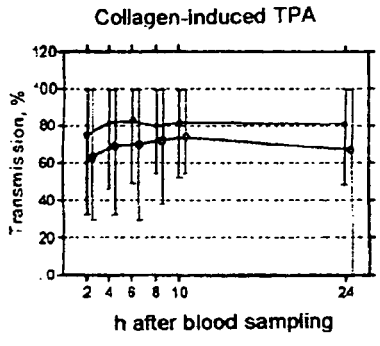
Figure 8F:
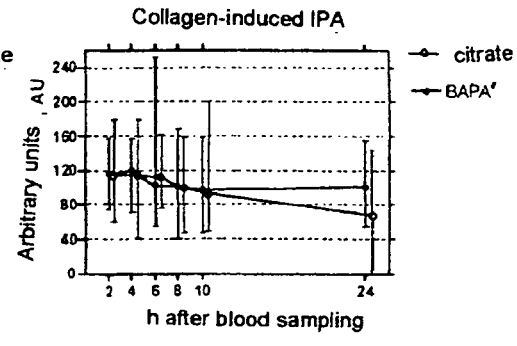

FIG. 7 shows the formation of the prothrombin fragment F1+2 (F1+2) after the anticoagulation of human vein blood with BAPA' (concentration in the anticoagulated blood=500 μM, 50 μM and 5.0 μM).

FIGS. 8a-8f show the thrombocyte aggregation induced by different agonists in blood anticoagulated with BAPA' or citrate. In the legend TPA means: Turbidimetric platelet aggregation, IPIA: Impedance-full blood platelet aggregation and AA: arachidonic acid.

Figure 9A:
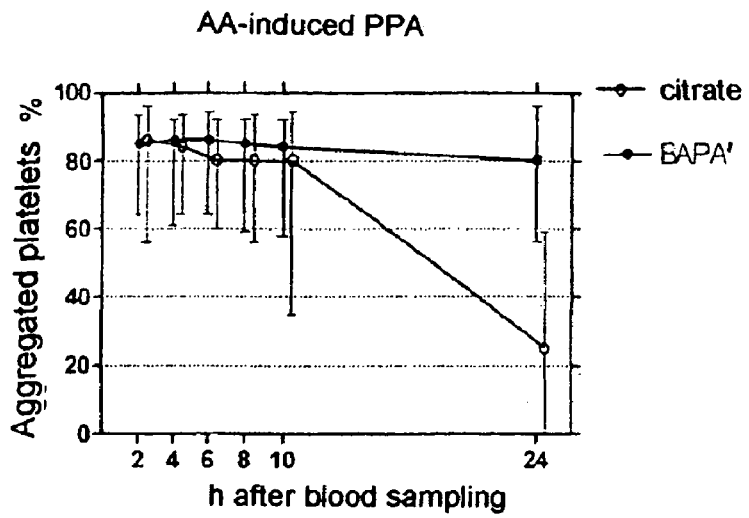
Figure 9B:
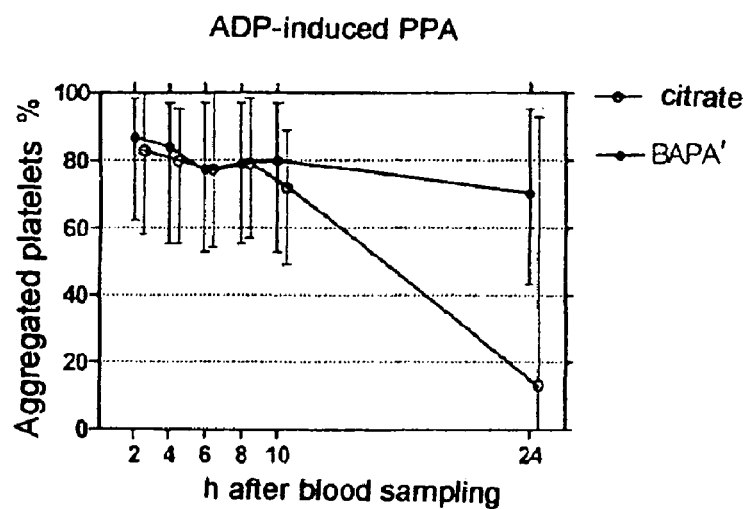
Figure 9C:
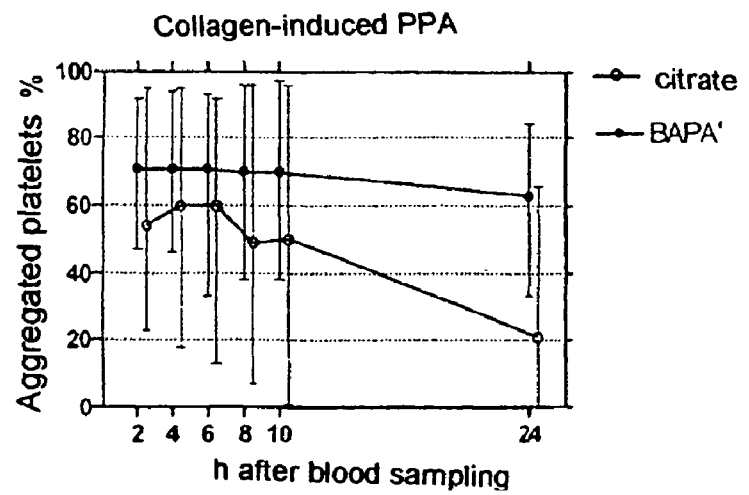

FIGS. 9a-9c show the proportion of aggregated thrombocytes (platelets) in blood anticoagulated with BAPA' or citrate, the thrombocyte aggregation being induced with different agonists. In the legend PPA means: particle number platelet aggregation and AA: arachidonic acid.

Figure 10A:
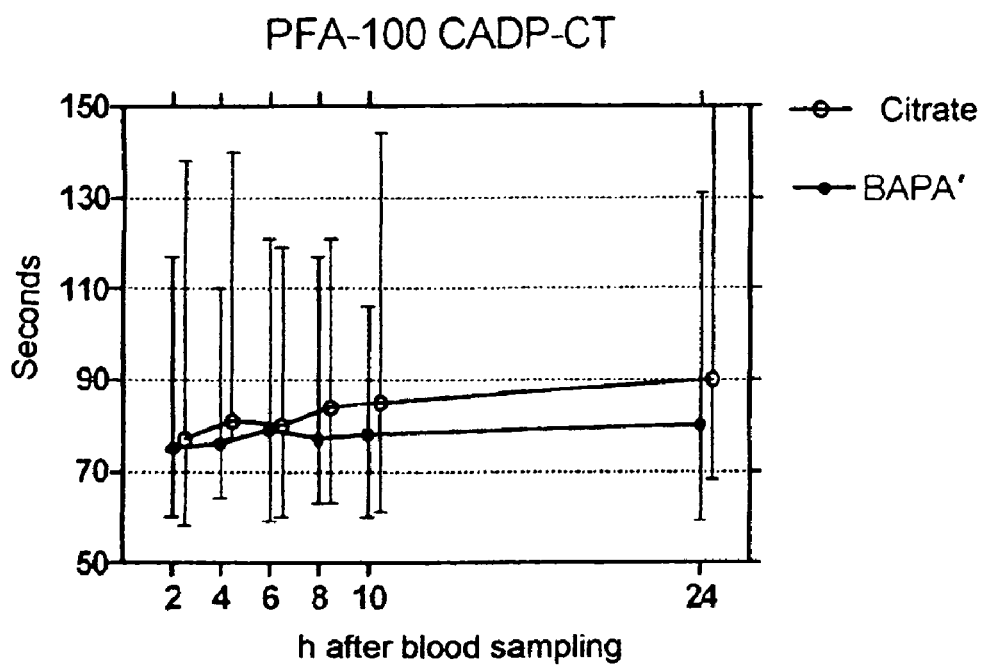
Figure 10B:
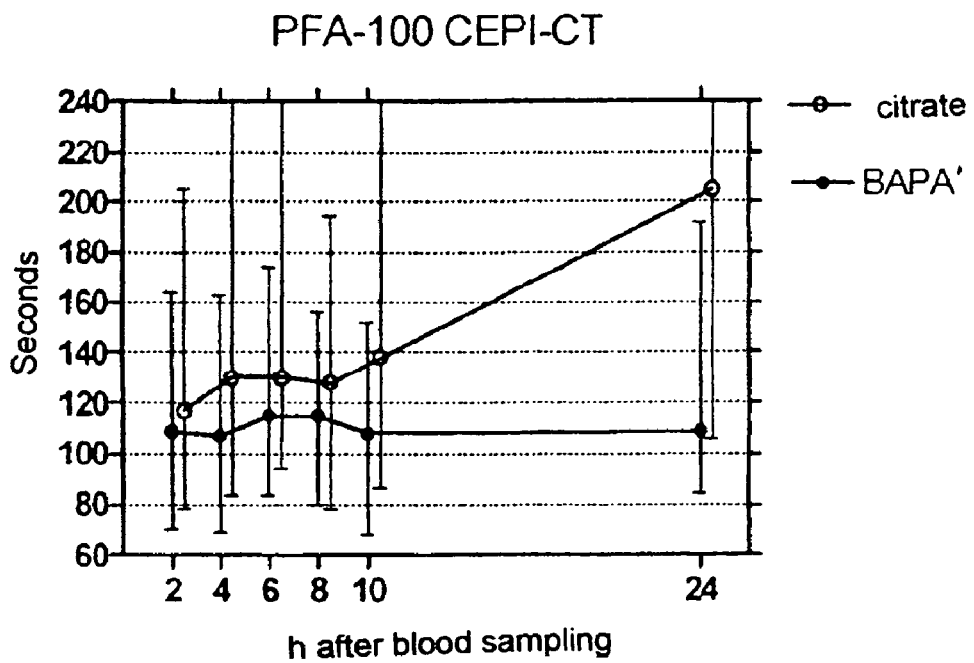

FIGS. 10a-10b show the closure times of blood anticoagulated with BAPA' or citrate for membranes coated with different agonists. In the legend CADP means: collagen-ADP, CEPI: collagen-epinephrin, CT: Closure Time, and PFA-100: Platelet Function Analyser 100.

Example 1

Inhibitory Action of Inhibitors Used by Way of Example on Human Coagulation Factors Xa, VIIa, XIa, XIIa and Plasma-kallikrein (PK)

The inhibitors used here are the commercially available exemplary inhibitors Pefabloc tPA/Xa (2,7-bis(4-amidinobenzylidene)-cyclopeptanone-(1), Pentapharm Ltd. Basel, Switzerland), CJ-FXa (benzylsulphonyl-D-arginyl-glycyl-4-amidinobenzylamide, Haemochrom GmbH, Essen, Germany) and CJ-PK (benzylsulphonyl-D-seryl-carbobenzoxylsyl-4-amidinobenzylamide, Haemochrom GmbH, Essen, Germany). Research samples were available of DX-9065a ((+)-(2S)-2-[4-[[3S)-1-acetimidoyl-3-pyrrodinyl]oxy]phenyl]-3-[7-amidino-2-naphthyl]propanic acid, Daiichi Pharmaceutical Company Ltd., Tokyo, Japan), and Otamixaban (2-(R)-(3-carbamimidoylbenyzyl)-3-(R)-[4-(1-oxypyridin-4-yl)benzoylamino]-butyric acid-methylester, Sanofi-Aventis GmbH, Frankfurt, Germany), both of which are undergoing clinical tests. In order to examine the inhibitory action of these exemplarily used inhibitors on the blood coagulation factors plasma-kallikrein, VIIa, Xa, XIa and XIIa, the $K_i$ values of the respective enzyme-inhibitor complexes were determined.

The determination of the $K_i$ values was carried out at 25° C. in tris buffer (0.05 mol/l, pH 8.0; contains 0.154 mol/l NaCl and 5% ethanol). The enzymes were produced by Haemochrom Diagnostica GmbH (Essen, D) and were dissolved in 0.154 mol/l NaCl. The substrates (Pentapharm AG, Basel, CH) were dissolved in $H_2O$ and the inhibitor was dissolved in the above-mentioned tris buffer. The following substrates were used for the individual enzymes:

| Enzyme | Substrate | |
|---|---|---|
| | Chemical name | Commercial name |
| Plasma-kallikrein | Bz-Pro-Phe-Arg-pNA | Chromozym PK |
| Factor VIIa | $CH_3SO_2$-D-phe-Gly-Arg-pNA | Chromozym tPA |
| Factor Xa | $CH_3OCO$-D-Cha-Gly-Arg-pNA | Pefachrome Fxa |
| Factor XIa | H-D-Lys(Cbo)-Pro-Arg-pNA | Chromozym Pca |
| Factor XIIa | H-D-HHT-Gly-Arg-pNA | Chromozym XII |

Bz = benzyl-,
Lys(Cbo) = Omega-carbobenzoxylysin,
HHT, hexahydrothyrosin,
Cha, cyclohexylalanine,
pNA = para-nitroaniline 200 μl of inhibitor solution were mixed with 25 μl of substrate for the determination and the reaction was started by the addition of 50 μl of enzyme. After a reaction time of 3-5 mins. 25 μl of acetic acid (50%) were added and the extinction was measured at 405 nm with a microplate reader (iEMS Reader MF 12401, Labsystems, Helsinki, Finland). The evaluation was carried out graphically according to Dixon (Biochem. J., 55, 170, 1953).

The $K_i$ values determined for the inhibitors used by way of example are shown in Table 1.

TABLE 1

| | $K_i$ (μM) | | | | |
|---|---|---|---|---|---|
| Inhibitor | Factor Xa | Factor VIIa | Factor XIa | Factor XIIa | PK |
| DX-9065a | 0.007 | 92 | 2.3 | 0.34 | 0.53 |
| Pefabloc tPA/Xa | 0.0051 | 140 | 42 | 0.36 | 0.72 |
| CJ-FXa | 0.0035 | 9.6 | 0.80 | 0.35 | 0.084 |
| CJ-PK | 2.9 | 3.8 | 0.25 | 12 | 0.0035 |
| Otamixaban | 0.00050 | 19 | 23 | >1000 | 0.026 |

PK = Plasma-kallikrein

Example 2

Inhibition of Thrombin Formation in Hirudin-anticoagulated Plasma after Activation by Means of Kaolin by Inhibitors of Blood Coagulation Factors In this example thrombin formation was activated in plasma anticoagulated with hirudin by the addition of kaolin and the ability of the inhibitors to inhibit thrombin formation was examined.

Blood sampled from a patient was initially anticoagulated by means of the thrombin inhibitor hirudin. For this purpose 9 parts of blood were mixed with 1 part of hirudin solution (recombinant hirudin HBW 023, Hoechst, Frankfurt, 2000 E/ml of physiological NaCl solution), then centrifuged for 10 minutes at 1300 revolutions per minute (rpm). 900 µl of the plasma anticoagulated with hirudin, present in excess, were mixed in polypropylene tubes with 50 µl of inhibitor solution or 0.9% NaCl solution and 50 µl kaolin suspension (from APTT-Test from Roche Diagnostics, diluted 1:250 before use with physiological NaCl solution), and incubated at 37° C. with light shaking. In this case kaolin acts as a non-physiological surface which activates the blood coagulation thereby finally stimulating thrombin formation. At certain times the quantity of the thrombin formed was determined immunologically on the basis of the formation of the prothrombin fragment F1+2 (Enzygnost F1+2 micro, Dade Behring GmbH, Marburg). This determination is based on an enzyme immunoassay according to the sandwich principle. For this purpose aliquot volumes (600 µl) were anticoagulated at certain times with 0.1 M EDTA (40 µl) and kept at −20° C. To determine the concentration of the prothrombin fragment F1+2 50 µl of plasma (if necessary diluted with PBS, phosphate-buffered saline) were incubated with monoclonal antibodies against the human prothrombin fragment F1+2, which were fixed on a microtitre plate included in the test kit. After a washing stage with PBS, which was used to remove sample material not bound by the antibodies, antibodies conjugated with peroxidase were incubated against human prothrombin binding to the free F1+2 determinants. After a further washing process, in which the unbound enzyme-conjugated antibodies are removed, Chromogen (o-phenylene diamine/$H_2O_2$ solution) was added in order to produce a colour reaction with the peroxidase bound to the antibodies against human prothrombin, the intensity of this reaction being proportional to the concentration of the prothrombin fragment F1+2 in the sample. This was then determined photometrically at a wavelength of 492 nm.

Figure 1:
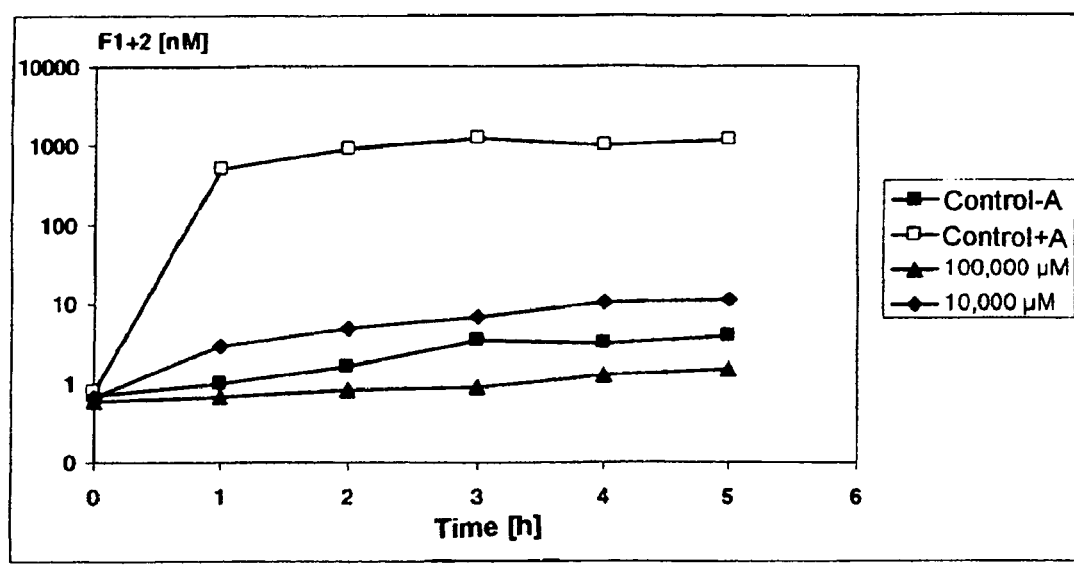
Figure 2:
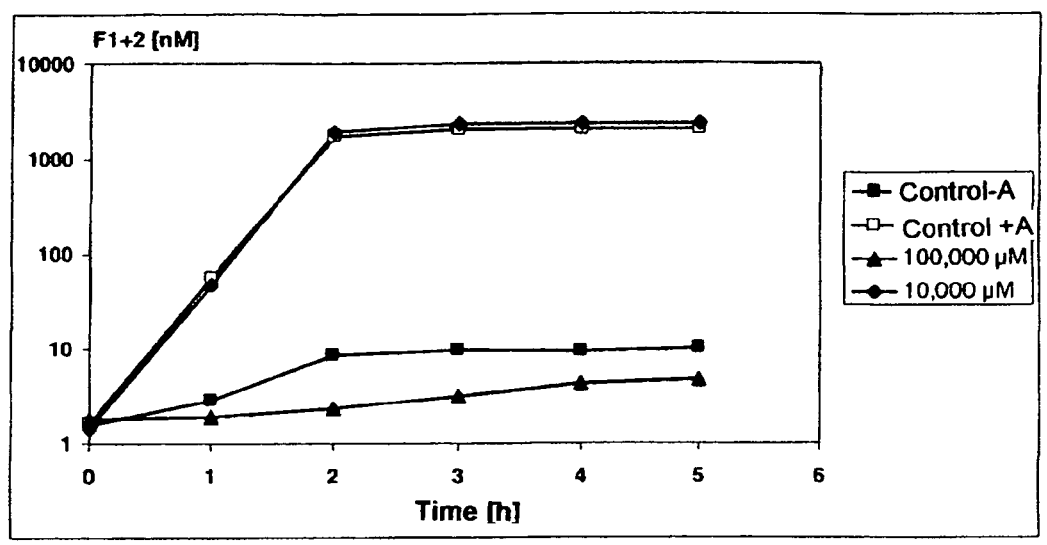
Figure 3:
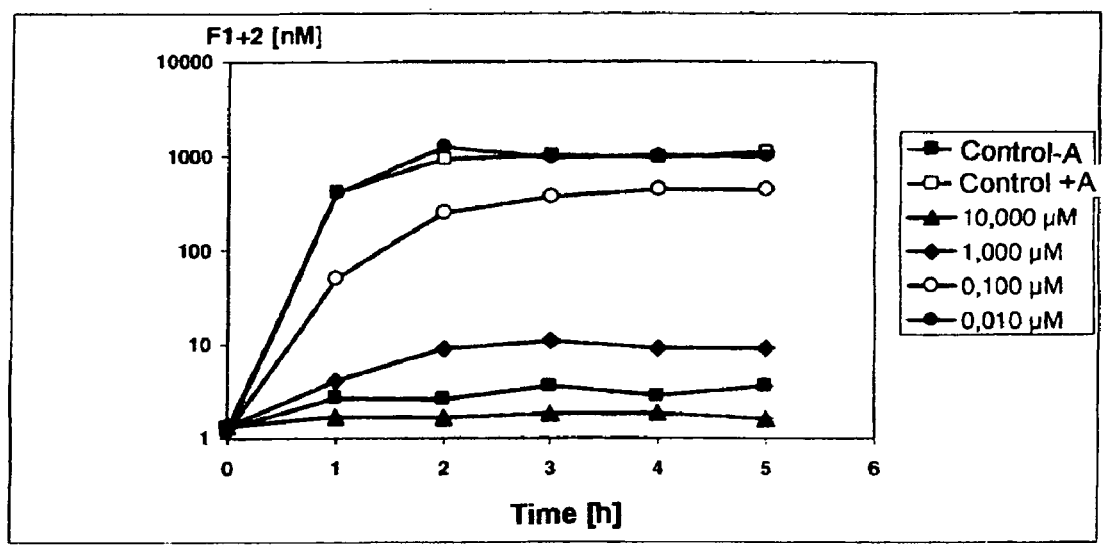

As can be seen from FIGS. 1 to 3, the exemplary inhibitors are capable of effectively suppressing the thrombin formation stimulated by the activation with kaolin. Thus inhibitors of the blood coagulation factor Xa, with $K_i$ values of up to 10 nM, as the inhibitor Pefabloc tPA/Xa (FIG. 1) shown by way of example in Table 1, are capable of totally suppressing thrombin formation at a concentration of 100 µM. Very strong inhibitors of the enzymes of the early phase of the coagulation, such as the plasma-kallikrein inhibitor CJ-PK (Table 1), also suppress thrombin formation effectively (FIG. 2) at a concentration of 100 µM. Substances which, like Otamixaban, inhibit the blood coagulation factor Xa with a $K_i$ value <0.1 nM (FIG. 3), are proving particularly suitable for blocking thrombin formation after kaolin activation. When interpreting the results obtained in this example consideration must be given to the fact that the tests in this example were not carried out in a physiological environment, but by using kaolin, which is a non-physiological strong activator of thrombin formation. These results therefore show, impressively, that blood plasma can be successfully anticoagulated despite the strong non-physiological activation of thrombin formation by kaolin using the inventive method.

Example 3

Storage of Human Vein Blood after Anticoagulation with Different Inhibitors

In this experiment it was determined how long human vein blood can be stored without the formation of thrombin or activation of thrombocytes.

For this purpose blood (9 parts) sampled from a patient was mixed with inhibitor solution (0.05 mM, 0.5 mM or 5 mM in physiological NaCl solution; 1 part). Some of the blood was stored at 25° C., the remainder in the refrigerator at 4° C. The quantity of thrombin formed was determined immunologically during storage based on the formation of the prothrombin fragment F1+2 (Enzygnost F1+2 micro, Dade Behring GmbH, Marburg). It was shown that the inhibitors CJ-FXa and Otamixaban, used by way of example, are capable of keeping anticoagulated blood uncoagulated at a concentration in the blood of 500 µM for more than 48 hours (Table 2). In this case it is irrelevant whether the blood samples were kept at room temperature (approx. 25° C.) or at 4° C. At a concentration of 50 µM Otamixaban prevents coagulation for over 24 hours, CJ-FXa only for approx. 24 hours.

Figure 4:
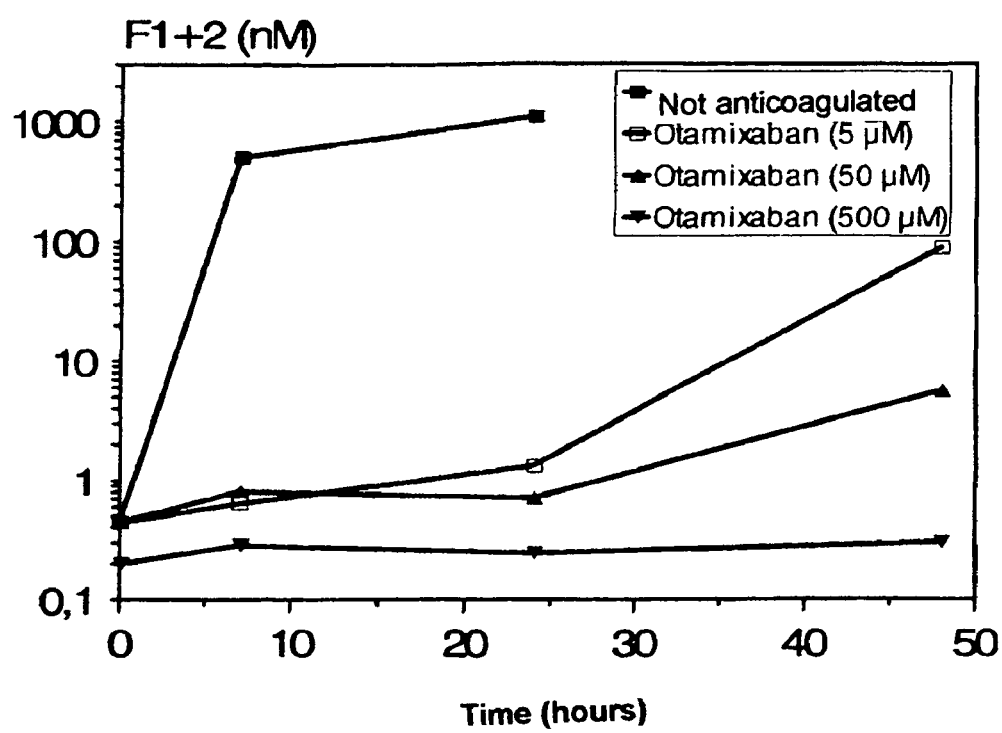
FIG. 4 shows the formation of the prothrombin fragment F1+2 (F1+2) after the anticoagulation of human vein blood with Otamixaban (concentration in the anticoagulated blood=500 μM, 50 μM and 5.0 μM).
Figure 5:
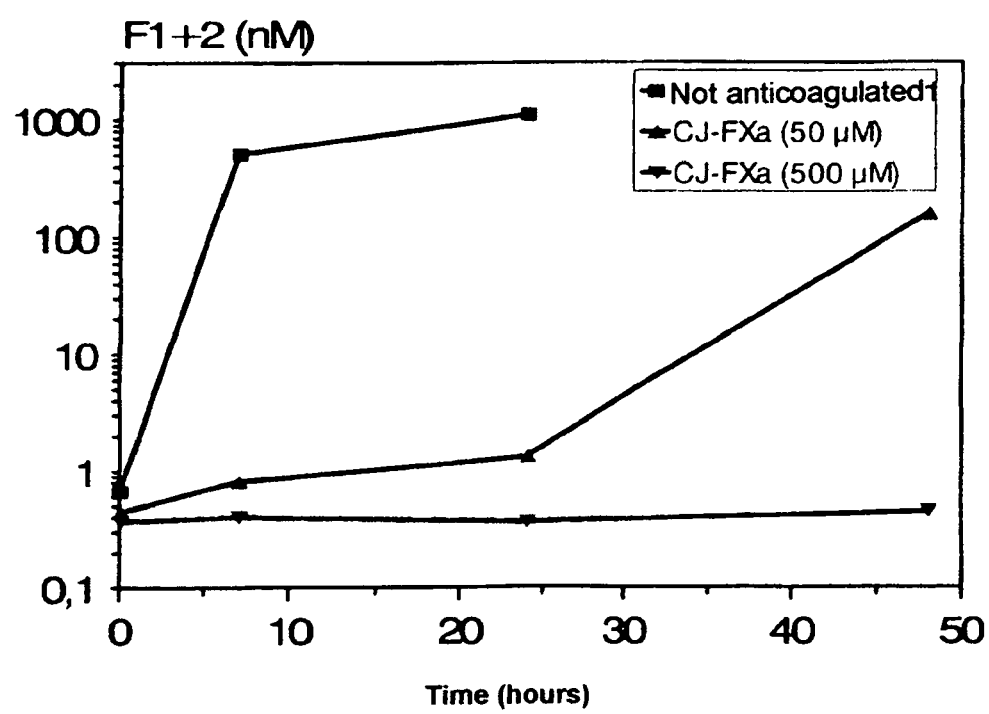
FIG. 5 shows the formation of the prothrombin fragment F1+2 (F1+2) after the anticoagulation of human vein blood with CJ-FXa (concentration in the anticoagulated blood=500 μM and 50 μM).

As shown by way of example for Otamixaban (FIG. 4) and CJ-FXa (FIG. 5), less than 1 nM of thrombin (evidence through F1+2 fragment) is newly formed in the respective period. The other inhibitors tested by way of example, DX-9065a and Pefabloc tPA/Xa, are not capable of preventing coagulation for more than 12 hours in the concentrations indicated.

TABLE 2

| Inhibitor | Concentration in the blood (µM) | Anticoagulation time (h) 4° C. | 25° C. |
|---|---|---|---|
| DX 9065a | 500 | n.d. (not determined) | 7-12 |
| DX 9065a | 50 | n.d. | 5-7 |
| Pefabloc tPA/Xa | 500 | n.d. | 7-10 |
| CJ-Fxa | 500 | >48 | >48 |
| CJ-Fxa | 50 | n.d. | 12-24 |
| CJ-FXa + CJ-PK | 50 each | n.d. | 24-32 |
| Otamixaban | 500 | >48 | >48 |
| Otamixaban | 50 | n.d. | 24-32 |
| Otamixaban | 5 | n.d. | 12-24 |

These results also show that the efficiency of the inventive method for the anticoagulation of human bloods ex vivo correlates positively with the $K_i$ value of the inhibitor of the blood coagulation factor Xa. It should also be noted at this point that the inventive method can be carried out with any direct inhibitor of the blood coagulation factor Xa. Thus the anticoagulation of human blood ex vivo can also be achieved with direct inhibitors of the blood coagulation factor Xa, which have $K_i$ values of over 10 nM. In these cases only the concentration of this inhibitor in the blood need be increased correspondingly. It is therefore often advantageous, for cost reasons for example, if stronger direct inhibitors of the blood coagulation factor Xa ($K_i$ value <10 nM) are used in lower concentrations.

Example 4

Induced Activation of the Thrombocytes after Anticoagulation with Direct Inhibitors of the Blood Coagulation Factor Xa In this experiment it is shown that the thrombocytes in the blood anticoagulated according to the invention can be activated without problem by induction, whilst this is not the case over a long period with blood anticoagulated with citrate.

For this purpose blood was taken within 1 hour from 12 healthy subjects. 1 aliquot of each of the 12 blood samples was anticoagulated with citrate and 1 other aliquot of the 12 blood samples was anticoagulated with a direct inhibitor of the blood coagulation factor Xa. For this purpose 9 parts of blood were mixed with 1 part of citrate (0.106 mol/l) or 1 part of inhibitor solution in a suitable concentration. Platelet-rich plasma (PRP) was manufactured by centrifuging at 164×g over 10 minutes. The thrombocytes in PRP were activated by induced aggregation according to Born with 5 µmols/l of ADP, 2 µg/ml of collagen and 0.5 mmol/l of arachidonic acid. Impedance full blood aggregometry was carried out with the Multiplate aggregometer and with 6.5 µmols/l of ADP, 3.2 µg/ml of collagen and 0.5 mmol/l of arachidonic acid. The analyses were conducted 1, 2, 3, 4, 5, 10 and 24 hours after blood sampling. Whilst the induced aggregations had dropped in the blood anticoagulated with citrate 24 hours after sampling to 20 to 30% of the initial value, the extent of the aggregation in the blood anticoagulated according to the invention did not vary.

24 hours after blood sampling 70% of the thrombocytes in the RPR anticoagulated according to the invention showed a normal propagation on plastic object carriers, just as 1 hour after blood sampling. On the contrary, less than 10% of the thrombocytes in RPR anticoagulated with citrate were still propagated 24 hours after blood sampling.

Example 5

Preservation and Storage of Thombocyte Apheresis Concentrates

In this experiment it is shown that blood products such as thrombocyte apheresis concentrates can be preserved and stored over a long period of time by employing the inventive method for the anticoagulation of human blood ex vivo.

A thrombocyte apheresis concentrate which consists of thrombocytes suspended in plasma was manufactured by thrombocyte apheresis by means of a commercially available cell separator using citrate initially as anticoagulant. A satellite bag, which contained calcium chloride and an inventive direct inhibitor of the blood coagulation factor Xa in physiological solution, was integrated in a closed thrombocyte apheresis bag system. Immediately after completion of the thrombocyte the solution in the satellite bag was added to the thrombocyte apheresis concentrate. The addition of calcium ions (recalcification) set a physiological calcium ion concentration in the thrombocyte apheresis concentrate which served to guarantee optimum thrombocyte function. The anticoagulation of the plasma, which is now coagulable again and in which the thrombocytes were suspended, was prevented according to the invention by adding the direct inhibitor of the blood coagulation factor Xa.

The thrombocyte apheresis concentrate was stored at 22±2° C. with constant agitation. After 10 days of storage the thrombocyte apheresis concentrate, which was anticoagulated according to the invention with a direct inhibitor of the blood coagulation factor Xa, was still as effective as conventional thrombocyte apheresis concentrates after 5 days.

Thus the thrombocyte apheresis concentrates anticoagulated according to invention still displayed the "swirling phenomenon" even after 10 days of storage (the "swirling phenomenon" is based on the diffusion of light of moved thrombocytes having a normal morphology, and disappears when the normally disc-shaped thrombocytes assume an abnormal, spherical shape), and had a pH value >6.7. In this case the thrombocyte number was always greater than $>2\times10^{11}$/unit. The aggregation of the thrombocytes was initiated by induction with 2 µg/ml of collagen, the maximum amplitude being 25%. Furthermore, the thrombocyte aggregation could also be induced with 5 or 10 µmols/l of ADP.

These results show that blood products can be preserved and stored by the inventive method for a long period of time without anticoagulation taking place and without this impairing the activatability of the thrombocytes.

Example 6

Synthesis of the Inventive Inhibitor BAPA'

The inhibitor according to formula (II), BAPA', used exemplarily for the subsequent tests, was synthesised by coupling of benzylsulphonyl-D-arg(Pbf)-OH (manufactured according to Schweinitz et al., Med. Chem. 2006, 2, 349-361) and H-pro-4-amidinobenzylamide×2HCl (manufactured according to WO 02/0959065), Pbf being a 2,2',4,6,7-pentamethyldihydro-benzofuran-5-sulphony protective group. For this purpose 0.5 g (0.861 mmol) of benzylsulphonyl-D-arg(Pbf)-OH and 289 mg (0.904 mmols) of H-pro-4-amidinobenzylamide×2HCl were dissolved in 15 ml of DMF. 326 mg (0.861 mmols) of 2-(1H-benzotriazol-1-yl)1,1,3,3-tetramethyluronium hexafluorophosphate and 300 µl (1.722 mmols) of diisopropylethylamine were added at 0° C. The mixture was agitated for 30 mins. at 0° C. and for a further 5 h at room temperature (22±2° C.). The solvent was removed with vacuum and the oily residue mixed with 10 ml of trifluoroacetic acid without further cleaning. After 1.5 h of agitation at room temperature (22±2° C.) the solvent was concentrated in a vacuum and the residue then mixed with ether. The precipitating raw product was separated with preparative RP-HPLC. The fractions which contained BAPA' were combined and lyophilised after partial removal of the solvent.

An HPLC system from Waters and a Saphir 110 column (10 µm C18) 50×300 mm from Grom were used for the preparative RP-HPLC. The detection took place at 220 nm. Water with 0.1% TFA (A) and acetonitrile with 0.1% TFA (B), at a flow rate of 10 or 20 ml/mn and at a suitable gradient, were used as eluent. The mass spectra were measured on a ZQ 4000 from Waters.

The synthesis produced a yield of BAPA' (molecular weight as 2×TFA salt 784.7 g/mol) of 295 mg (equivalent to 0.376 mmol).

The calculated molar mass is MS=556.26. A molar mass of MS=557.3 (M+H)$^+$ was found in the mass spectrum.

Example 7

Inhibitory Action of BAPA' on the Human Coagulation Factors Xa, VIIa, XIa, XIIa, Plasma Kallikrein (PK) and Thrombin In order to examine the inhibitory action of the exemplarily used inhibitor BAPA' on the blood coagulation factors plasma-kallikrein, VIIa, Xa, XIa, XIIa and thrombin, the $K_i$ values of the respective enzyme-inhibitor complexes were determined.

The determination of the $K_i$ values as carried out at 25° C. in tris buffer (0.05 mol/l, pH 8.0; contains 0.154 mol/l NaCl and 5% ethanol). The enzymes were produced by Haemochrom Diagnostica GmbH (Essen, D), and only thrombin was manufactured in our own laboratory according to Walsmann (Pharmazie 23, 401-402, 1968). All the enzymes were dissolved in 0.154 mol/l NaCl. The substrates (Pentapharm AG, Basel, CH) were dissolved in $H_2O$ and the inhibitor was dissolved in the above-mentioned tris buffer. The following substrates were used for the individual enzymes:

|  | Substrate |  |
| --- | --- | --- |
| Enzyme | Chemical name | Commercial name |
| Plasma-kallikrein | Bz-Pro-Phe-Arg-pNA | Chromozym PK |
| Factor VIIa | $CH_3SO_2$-D-phe-Gly-Arg-pNA | Chromozym tPA |
| Factor Xa | $CH_3OCO$-D-Cha-Gly-Arg-pNA | Pefachrome FXa |
| Factor XIa | H-D-Lys(Cbo)-Pro-Arg-pNA | Chromozym PCa |
| Factor XIIa | H-D-HHT-Gly-Arg-pNA | Chromozym XII |
| Thrombin | $CH_3SO_2$-D-HHT-gly-arg-pNA | Pefachrome tPA |

Bz = benzyl-,
Lys(Cbo) = Omega-carbobenzoxylysin,
HHT, hexahydrothyrosin,
Cha, cyclohexylalanine,
pNA = para-nitroaniline 200 µl of inhibitor solution were mixed with 25 µl of substrate for the determination and the reaction was started by the addition of 50 µl of enzyme. After a reaction time of 3-5 mins. 25 µl of acetic acid (50%) were added and the extinction was measured at 405 nm with a microplate reader (iEMS Reader MF 1401, Labsystems, Helsinki, Finland). The evaluation was carried out graphically according to Dixon (Biochem. J., 55, 170, 1953).

The $K_i$ values determined for BAPA' are shown in Table 3.

TABLE 3

| | $K_i$ (µM) | | | | | |
| --- | --- | --- | --- | --- | --- | --- |
| Inhibitor | Factor Xa | Factor VIIa | Factor XIa | Factor XIIa | PK | Thrombin |
| BAPA' | 0.0024 | 0.83 | 0.027 | 0.13 | 0.0083 | 0.0035 |

PK = Plasma-kallikrein

Example 8

Inhibition of Thrombin Formation in Hirudin-anticoagulated Plasma After Activation by Means of Kaolin by BAPA'

In this example thrombin formation was activated in plasma anticoagulated with hirudin by the addition of kaolin and the ability of the inhibitor BAPA' to inhibit thrombin formation was examined.

Blood sampled from a patient was initially anticoagulated by means of the thrombin inhibitor hirudin. For this purpose 9 parts of blood were mixed with 1 part of hirudin solution (recombinant hirudin HBW 023, Hoechst, Frankfurt, 2000 E/ml of physiological NaCl solution), then centrifuged for 10 minutes at 1300 revolutions per minute (rpm). 900 µl of the plasma anticoagulated with hirudin, present in excess, were mixed in polypropylene tubes with 50 µl of inhibitor solution or 0.9% NaCl solution and 50 µl kaolin suspension (from APTT-Test from Roche Diagnostics, diluted 1:250 before use with physiological NaCl solution), and incubated at 37° C. with light shaking. In this case kaolin acts as a non-physiological surface which activates the blood coagulation thereby finally stimulating thrombin formation. At certain times the quantity of the thrombin formed was determined immunologically on the basis of the formation of the prothrombin fragment F1+2 (Enzygnost F1+2 micro, Dade Behring GmbH, Marburg). This determination is based on an enzyme immunoassay according to the sandwich principle. For this purpose aliquot volumes (600 µl) were anticoagulated at certain times with 0.1 M EDTA (40 µl) and kept at −20° C. To determine the concentration of the prothrombin fragment F1+2 50 µl of plasma (if necessary diluted with PBS, phosphate-buffered saline) were incubated with monoclonal antibodies against the human prothrombin fragment F1+2, which were fixed on a microtitre plate included in the test kit. After a washing stage with PBS, which was used to remove sample material not bound by the antibodies, antibodies conjugated with peroxidase were incubated against human prothrombin binding to the free F1+2 determinants. After a further washing process, in which the unbound enzyme-conjugated antibodies are removed, Chromogen (o-phenylene diamine/$H_2O_2$ solution) was added in order to produce a colour reaction with the peroxidase bound to the antibodies against human prothrombin, the intensity of this reaction being proportional to the concentration of the prothrombin fragment F1+2 in the sample. This was then determined photometrically at a wavelength of 492 nm.

As can be seen from FIG. 6, BAPA' is capable of effectively suppressing the thrombin formation stimulated by the activation with kaolin. BAPA', which inhibits the blood coagulation factor Xa with a K value of 2.4 nM (Table 3), is still capable of blocking thrombin formation after kaolin activation >97% at a concentration of 0.1 µM.

When interpreting the results obtained in this example consideration must be given to the fact that the tests in this example were not carried out in a physiological environment, but by using kaolin, which is a non-physiological strong activator of thrombin formation. These results therefore show, impressively, that blood plasma can be successfully anticoagulated despite the strong non-physiological activation of thrombin formation by kaolin using the inventive method.

Example 9

Storage of Human Vein Blood after Anticoagulation BAPA'

In this experiment it was determined how long human vein blood can be stored without the formation of thrombin or activation of thrombocytes.

For this purpose blood (9 parts) sampled from a patient was mixed with inhibitor solution (0.05 mM, 0.5 mM or 5 mM in physiological NaCl solution; 1 part) and stored at room temperature (about 22±2° C.). The quantity of thrombin formed was determined immunologically during storage based on the formation of the prothrombin fragment F1+2 (Enzygnost F1+2 micro, Dade Behring GmbH, Marburg). It was shown that BAPA' is capable of keeping anticoagulated blood uncoagulated at a concentration in the blood of 500 µM or 50 µM for more than 48 hours (Table 4). At a concentration of 5 µM BAPA' prevents coagulation for more than 8 hours.

As has been shown by way of example (FIG. 7) less than 1 nM of thrombin (evidence from F1+2 fragment) is newly formed during the period concerned.

TABLE 4

| Inhibitor | Concentration in the blood (µM) | Anticoagulation time (h) |
|---|---|---|
| BAPA' | 500 | 48 |
| BAPA' | 50 | 48 |
| BAPA' | 5 | 8 |

Example 10

Induced Activation of the Thrombocytes after Anticoagulation with 'BAPA'

In this experiment it is shown that the thrombocytes in the blood anticoagulated according to the invention can be activated without problem by induction, whilst this is not the case over a long period with blood anticoagulated with citrate.

The tests described below were carried out on 12 women and 12 men who had not taken any aspirin or other medicines associated with impairment of the thrombocyte function within the last 14 days before blood sampling. Subjects with a history of increased tendency to haemorrhage were excluded. Two different series of tests were carried out, anticoagulation by means of citrate being conducted in the first test series and anticoagulation by means of the inventive inhibitor BAPA's being conducted in the other test series.

After 30 minutes rest in the sitting position blood was taken from the cubital vein of the subjects within 2 hours with a 21-gauge butterfly needle, with as little congestion as possible. The blood sampled was on the one hand aspirated in Monovettes (from Sarstedt), which contained 0.106 mol/l trisodium citrate (final ratio: 1 part of citrate to 9 part of blood), and was on the other hand aspirated in Monovettes which were prefilled with 500 µmols/l of BAPA' (final ratio: 1 part of BAPA' to 9 parts of blood). Blood and anticoagulant were carefully mixed by slight repeated tipping of the tubes. All the samples were stored at room temperature (22 ±2° C.). The analyses were conducted after 2, 4, 6, 8, 10 and 24 h.

a) Turbidimetric Platelet Aggregation (TPA)

In the TPA assay the transmission of light by the respective blood cell suspension was determined quantitatively by photometric measurement. Since PRP only has a low transmission for long-wave light due to the diffusion of light to the suspended individual thrombocytes, but PPP allows long-wave light to pass through almost unhindered, the relative percentage transmission of the light through the sample serves as a measure of the aggregation of the thrombocytes. An aggregation of the thrombocytes results in a reduction in the number of light diffusing particles and therefore allows the transmission of the sample to increase compared with PRP with non-aggregated thrombocytes.

Platelet-rich and platelet-poor plasma (PRP and PPP respectively) was manufactured for the TPA assays. Plate-let rich plasma was obtained by centrifuging the anticoagulated blood 2, 4, 6, 8, 109 and 24 h after sampling for 10 minutes at 15×g, and the excess was then removed. Platelet-poor plasma was obtained by 10 minutes of centrifuging at 3,500 g and removal of the excess. The number of platelets was not set.

The thrombocyte aggregation in PRP was stimulated for the TPA assays by the addition of arachidonic acid (AA), ADP or collagen. For this purpose 25 µl of arachidonic acid or ADP were added to 225 µl of PRP (final concentration of AA=0.5 mmol/l or of ADP=5 µmols/l) or 10 µl of collagen from horse sera were added to 240 µl of PRP (final concentration of collagen=2 µg/ml).

The aggregation of the individual samples was recorded for 7 minutes by means of an APACT 4 aggregometer (Labitec, Arensburg). The difference in light transmission between PRP and PPP was set equal to 100% on a linear scale as a reference. The maximum transmission variation in the PRP sample caused by the induced platelet aggregation was then recorded. The results are shown in FIG. 8.

b) Impedance Full Blood Platelet Aggregation (IPA).

Impedance full blood platelet aggregometry is based on the measurement of the variation in electrical resistance between two platinum electrodes as a result of the adsorption of thrombocytes in flow. The variation in resistance is in this case proportional to the thrombocyte aggregation.

300 µl of anticoagulated full blood were diluted with 300 µl of physiological sodium chloride solution and preheated for 3 minutes at 37° C. 20 µl of the agonists were then added to obtain final concentrations of 0.5 mmol/l of AA, 6.5 µmols/l of ADP and 333.2 µg/ml of collagen. The IPA assays were carried out with a Multiplate analyser (Instrumentation Laboratory, Kirchheim). The maximum aggregation was recorded 2, 4, 6, 8, 10 and 24 h after blood sampling for 6 minutes and expressed in arbitrary units (AU). The results are also shown in FIG. 8.

c) Particle Number Platelet Aggregation (PPA).

For particle number platelet aggregation, 1 ml of anticoagulated full blood was mixed with 1 ml of 0.1% (w/w) glutaraldehyde in saline phosphate buffer, pH 7.4, 2, 4, 6, 8, 10 and 24 h after sampling. In this sample the initial thrombocyte number was determined (ADVIA Analyser, Bayer Vital, Fernwald). 20 µl of agonist were introduced into a second tube to obtain final concentrations of 0.5 mmol/l of AA, 20 µmols/l of ADP and 4 µg/ml of collagen in 1 ml of anticoagulated full blood. The samples were then placed on a blood count agitator for mixing. 1 ml of glutaraldehyde buffer was then added, followed by a 3 minute wait, thoroughly mixed and the thrombocyte number was determined. The proportion of aggregated thrombocytes in % was calculated using the following formula:

[(Number of thrombocytes in the tube without agonist–number of thrombocytes in the tube with agonist)/number of thrombocytes in the tube without agonist]*100.

The results are shown in FIG. 9.

d) Measurement of Closure Times

The closure times, CT, were measured with the Platelet Function Analyser 100 (PFA-100). In this case measuring cells with membranes coated with different agonists were filled with anticoagulated full blood. The thrombocytes were deposited on the membranes where the aggregation of the thrombocytes was activated by contact with the agonists. The aggregation induced thereby resulted in a reduction in blood flows. The PFA-100 determined the time until complete membrane closure (closure time). The collagen-epinephrin (CEPI) and collagen-ADP (CADP) cartridges were used as measuring cells. The results are shown in FIG. 10.

The studies carried out in Example 10 show that a much higher storage stability of the samples, in terms of thrombocyte aggregability, can be achieved by anticoagulation with the inventive inhibitor compared to citrate. Using the inventive method it is therefore possible to preserve and store blood products over a long period of time without anticoagulation taking place and without therefore impairing the activatability of the thrombocytes.

Example 11

Preservation and Storage of Thombocyte Apheresis Concentrates

In this experiment it is shown that blood products such as thrombocyte apheresis concentrates can be preserved and stored over a long period of time by employing the inventive method for the anticoagulation of human blood ex vivo.

A thrombocyte apheresis concentrate which consists of thrombocytes suspended in plasma was manufactured by thrombocyte apheresis by means of a commercially available cell separator using citrate initially as anticoagulant. A satellite bag, which contained calcium chloride and an inventive direct inhibitor of the blood coagulation factor Xa in physiological solution, was integrated in a closed thrombocyte apheresis bag system. Immediately after completion of the thrombocyte apheresis the solution in the satellite bag was added to the thrombocyte apheresis concentrate. The addition of calcium ions (recalcification) set a physiological calcium ion concentration in the thrombocyte apheresis concentrate which served to guarantee optimum thrombocyte function. The anticoagulation of the plasma, which is now coagulable again and in which the thrombocytes were suspended, was prevented according to the invention by adding the direct inhibitor of the blood coagulation factor Xa.

The thrombocyte apheresis concentrate was stored at 22±2° C. with constant agitation. After 10 days of storage the thrombocyte apheresis concentrate, which was anticoagulated according to the invention with a direct inhibitor of the blood coagulation factor Xa, was still as effective as conventional thrombocyte apheresis concentrates after 5 days.

Thus the thrombocyte apheresis concentrates anticoagulated according to invention still displayed the "swirling phenomenon" even after 10 days of storage (the "swirling phenomenon" is based on the diffusion of light of moved thrombocytes having a normal morphology, and disappears when the normally disc-shaped thrombocytes assume an abnormal, spherical shape), and had a pH value >6.7. In this case the thrombocyte number was always greater than >2×10$^{11}$/unit. The aggregation of the thrombocytes was initiated by induction with 2 µg/ml of collagen, the maximum amplitude being 25%. Furthermore, the thrombocyte aggregation could also be induced with 5 or 10 µmols/l of ADP.

These results show that blood products can be preserved and stored by the inventive method for a long period of time without anticoagulation taking place and without this impairing the activatability of the thrombocytes.

The invention claimed is:

1. An inhibitor of blood coagulation factor Xa comprising a compound of formula (I):

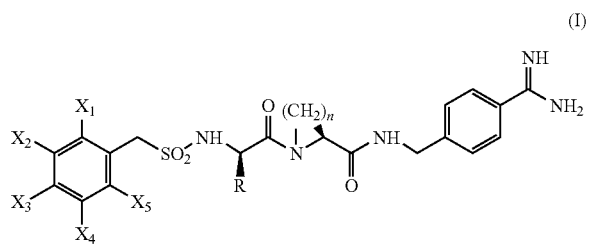

(I)

or a salt with acids thereof,
wherein
n is 2, 3 or 4,
R is —(CH$_2$)$_m$—NH—Y, wherein m is 1, 2, 3, 4 or 5, and Y is H or

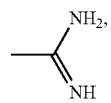

and X$_1$, X$_2$, X$_3$, X$_4$, X$_5$ are, independently, H, F, Cl, Br, I, NO$_2$, NH$_2$, OH, alkyl or alkoxy.

2. The inhibitor according to claim 1 or a salt with acids thereof, wherein
n is 3 or 4,
m is 2, 3 or 4, Y is H or

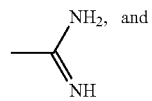

X$_1$, X$_2$, X$_3$, X$_4$, X$_5$ are independently H, F, Cl, Br, I, NO$_2$, NH$_2$, OH, alkyl or alkoxy.

3. The inhibitor according to claim 1 or a salt with acids thereof, wherein
n is 3, m is 3, Y is

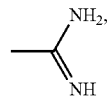

and X$_1$, X$_2$, X$_3$, X$_4$, X$_5$ are each H, or
n is 2, m is 3, Y is

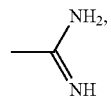

and X$_1$, X$_2$, X$_3$, X$_4$, X$_5$ are each H, or
n is 3, m is 4, Y is H and X$_1$, X$_2$, X$_3$, X$_4$, X$_5$ are each H, or
n is 3, m is 3, Y is

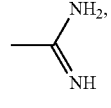

X$_1$, X$_2$, X$_4$, X$_5$ are each H, and X$_3$ is Cl.

4. The inhibitor according to claim 3 or a salt with acids thereof, wherein
n is 3,
m is 3, Y is

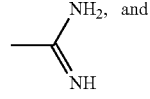

X$_1$, X$_2$, X$_3$, X$_5$ are each H.

5. A method for anticoagulation of human blood ex vivo, comprising adding at least one inhibitor according to claim 1 or a salt with acids thereof to the blood.

6. The method according to claim 5, wherein at least one inhibitor or a salt with acids thereof is present in physiological NaCl solution; or a buffer solution with a physiological ionic strength, a physiological pH value, or both.

7. A tube for taking blood samples, comprising a tube and an inhibitor according to claim 1 or a salt with acids thereof.

8. An apheresis hose/bag system, comprising at least one collection bag for receiving blood, wherein the collection bag has an effective quantity of an inhibitor according to claim 1 or a salt with acids thereof.

9. An infusion comprising
 a) a thrombocyte concentrate,
 b) the inhibitor according to claim 1 or a salt with acids thereof, and
 c) a sterile collection bag.

10. A kit for testing cellular blood components, comprising an inhibitor of the blood coagulation factor Xa according to claim 1 and a means for testing cellular blood components.

11. The kit according to claim 10, wherein the means for testing cellular blood components is a means for thrombocyte function diagnosis.

* * * * *